(12) United States Patent
Geldwert

(10) Patent No.: US 11,103,291 B2
(45) Date of Patent: Aug. 31, 2021

(54) SURGICAL IMPLANT FOR CORRECTION OF HALLUX VALGUS OR TAILOR'S BUNION

(71) Applicant: Josef J. Geldwert, New York, NY (US)

(72) Inventor: Josef J. Geldwert, New York, NY (US)

(*) Notice: Subject to any disclaimer, the term of this patent is extended or adjusted under 35 U.S.C. 154(b) by 346 days.

(21) Appl. No.: 15/367,969

(22) Filed: Dec. 2, 2016

(65) Prior Publication Data
US 2017/0079701 A1 Mar. 23, 2017

Related U.S. Application Data

(63) Continuation of application No. PCT/US2015/033893, filed on Jun. 3, 2015.

(60) Provisional application No. 62/007,279, filed on Jun. 3, 2014, provisional application No. 62/091,253, filed on Dec. 12, 2014.

(51) Int. Cl.
| | | |
|---|---|---|
| *A61B 17/80* | (2006.01) | |
| *A61B 17/84* | (2006.01) | |
| *A61B 17/88* | (2006.01) | |
| A61B 17/56 | (2006.01) | |
| A61B 17/17 | (2006.01) | |

(52) U.S. Cl.
CPC ...... *A61B 17/8061* (2013.01); *A61B 17/8004* (2013.01); *A61B 17/8085* (2013.01); *A61B 17/842* (2013.01); *A61B 17/8866* (2013.01); A61B 17/1728 (2013.01); A61B 17/1775 (2016.11); A61B 2017/565 (2013.01)

(58) Field of Classification Search
CPC ............ A61B 17/8061; A61B 17/8076; A61B 17/8085; A61B 17/8004; A61B 17/8019; A61B 17/82; A61B 17/823; A61B 17/826; A61B 17/8071
See application file for complete search history.

(56) References Cited

U.S. PATENT DOCUMENTS 4,377,872 A * 3/1983 Daniell, Jr. ............. A41F 9/002
2/321
5,415,661 A * 5/1995 Holmes ............... A61B 17/7026
606/255

(Continued)

FOREIGN PATENT DOCUMENTS

WO 2013154697 A1 10/2013

OTHER PUBLICATIONS

Extended European Search Report issued in European Patent Application No. 15803642.6 dated Jan. 8, 2018.
(Continued)

*Primary Examiner* — Amy R Sipp
(74) *Attorney, Agent, or Firm* — Heslin Rothenberg Farley & Mesiti PC

(57) ABSTRACT

Methods and devices for correcting hallux valgus and tailor's bunion are disclosed. An implant includes a bone engaging feature on each end connected by an intermediate portion. The implant is configured to be positioned on the dorsal side of the metatarsals and stabilizes two adjacent metatarsals toward one another, thereby decreasing the intermetatarsal angle. Depending on the severity of the deformity, a single or multiple implants may be used. In addition, the implant may be used as an adjunctive device in combination with other surgical procedures.

25 Claims, 32 Drawing Sheets

(56) References Cited

U.S. PATENT DOCUMENTS

| | | | | |
|---|---|---|---|---|
| 5,454,812 A | * | 10/1995 | Lin | A61B 17/7022 |
| | | | | 606/252 |
| 5,725,582 A | * | 3/1998 | Bevan | A61B 17/7022 |
| | | | | 606/263 |
| 6,214,005 B1 | * | 4/2001 | Benzel | A61B 17/7059 |
| | | | | 606/250 |
| 2003/0153947 A1 | * | 8/2003 | Koseki | A61B 17/06 |
| | | | | 606/228 |
| 2006/0235396 A1 | * | 10/2006 | Sanders | A61B 17/8061 |
| | | | | 606/280 |
| 2006/0235405 A1 | * | 10/2006 | Hawkes | A61B 17/7008 |
| | | | | 606/70 |
| 2006/0259076 A1 | | 11/2006 | Burkhart et al. | |
| 2007/0276383 A1 | * | 11/2007 | Rayhack | A61B 17/8019 |
| | | | | 606/86 B |
| 2009/0275989 A1 | * | 11/2009 | Linares | A61B 17/72 |
| | | | | 606/286 |
| 2010/0211071 A1 | | 8/2010 | Lettmann et al. | |
| 2010/0217328 A1 | | 8/2010 | Terrill et al. | |
| 2013/0138150 A1 | | 5/2013 | Baker et al. | |
| 2014/0081336 A1 | | 3/2014 | Zeester et al. | |

OTHER PUBLICATIONS

International Search Report and Written Opinion issued in PCT Application No. PCT/US2015/033893 dated Aug. 19, 2015.

* cited by examiner

SURGICAL IMPLANT FOR CORRECTION OF HALLUX VALGUS OR TAILOR'S BUNION

CROSS REFERENCE TO RELATED APPLICATIONS

This application is a continuation of PCT Application No. PCT/US2015/033983 filed on Jun. 3, 2015, which claimed priority benefit of U.S. Provisional Application No. 62/007,279 filed Jun. 3, 2014 and U.S. Provisional Application No. 62/091,253 filed Dec. 12, 2014, which are incorporated herein by reference in their entireties.

BACKGROUND

Aspects herein relate to a surgical implant for correction of hallux valgus or tailor's bunion. Methods of correcting hallux valgus and tailor's bunion using a surgical implant are also described herein.

Hallux valgus, commonly known as a bunion, is a condition or deformity in which the big toe points toward the second toe, resulting in a protrusion at the metatarsophalangeal (MTP) joint of the first metatarsal.

Tailor's bunion, also known as a bunionette, is a similar condition or deformity in which the fifth toe points toward the fourth toe, resulting in a protrusion at the MTP joint of the fifth metatarsal.

Non-surgical treatment of hallux valgus includes externally applied devices such as orthotics, bunion pads, arch supports, and braces. Surgical procedures to correct bunions include arthroplasty, osteotomy, and arthrodesis. Conventional implantable devices include an artificial joint that replaces all or part of the MTP joint and a suture-button construct that passes through and between the first and second metatarsal bones to laterally tension the first metatarsal bone towards the second metatarsal bone.

SUMMARY OF INVENTION

It has been found that the use of conventional suture-button implants gives rise to a high incidence of complications, including loosening of knots, stress fractures, stress risers, and recurrence of hallux valgus and/or tailor's bunion. Suture-button constructs invasively pass through the metatarsal bones, which may contribute to these complications.

It is appreciated that such complications may be reduced with the use of a less invasive implant that does not pass through the metatarsal bones. Accordingly, the implants described herein may at least partially wrap around the metatarsal bones rather than pass through them, and may be positioned on only the dorsal side of the metatarsal bones, enabling a less invasive and more comfortable arrangement.

According to one aspect, an implant for repositioning bones of a patient to a more anatomically correct position is provided. The implant includes a first bone engaging feature configured to wrap partially around the first bone, a second bone engaging feature configured to wrap partially around the second bone, and an intermediate portion connecting the first and second bone engaging features, the intermediate portion and the bone engaging features cooperating to enable the first bone to be drawn toward the second bone.

According to one aspect, a method of repositioning bones of a patient to a more anatomically correct position is provided. The method includes engaging a first bone engaging feature to a first bone such that the first bone engaging feature partially wraps around the first bone, engaging a second bone engaging feature to a second bone such that the second bone engaging feature partially wraps around the second bone, and drawing the first bone toward the second bone with an intermediate portion that connects the first and second bone engaging features.

According to another aspect, an implant for repositioning bones of the patient to a more anatomically correct position is provided. The implant includes a first bone engaging feature configured to engage a first bone, a second bone engaging feature configured to engage a second bone, an intermediate portion connecting the first and second bone engaging features, the intermediate portion and the bone engaging features cooperating to enable the first bone to be drawn toward the second bone, wherein the intermediate portion is arranged such that, when the implant is engaged with the first and second bones, the intermediate portion is located only dorsal to metatarsals of a foot of the patient.

According to one aspect, an implant for repositioning bones of the patient to a more anatomically correct position is provided. The implant includes a first bone engaging feature shaped to wrap partially around a first bone, a second bone engaging feature shaped to wrap partially around a second bone and an intermediate portion connecting the first and second bone engaging features. The intermediate portion and the bone engaging features cooperate to enable the first bone to be drawn toward the second bone. The intermediate portion includes a flexure feature that permits relative movement of the first and second bone engaging features.

According to one aspect, an implant for repositioning bones of the patient to a more anatomically correct position is provided. The implant includes a first bone engaging feature for engaging a first bone, a second bone engaging feature for engaging a second bone and an intermediate portion connecting the first and second bone engaging features. The intermediate portion and the bone engaging features cooperating to enable the first bone to be drawn toward the second bone. The intermediate portion includes a flexure feature that permits relative movement of the first and second bone engaging features. In addition, the flexure feature is arranged such that, when the implant is engaged with the first and second bones, the flexure feature is located substantially only dorsal or substantially only ventral to the metatarsals of the foot of the patient.

According to one aspect, an implant for repositioning bones of the patient to a more anatomically correct position is provided. The implant includes a first bone engaging feature shaped to engage a first bone, a second bone engaging feature shaped to engage a second bone and an intermediate portion connecting only the first and second bone engaging features. The intermediate portion and the bone engaging features cooperating to enable the first bone to be drawn toward the second bone. The intermediate portion is constructed and arranged such that, when the implant is engaged with the first and second bones, the intermediate portion is positioned substantially between the first and second bones without any portion of the implant passing entirely through either the first or second bones.

According to one aspect, an implant for repositioning bones of the patient to a more anatomically correct position is provided. The implant includes a first bone engaging feature shaped to engage a first bone, a second bone engaging feature shaped to engage a second bone and an intermediate portion connecting only the first and second bone engaging features. The intermediate portion and the bone engaging features cooperating to enable the first bone to be drawn toward the second bone. The first bone anchor hole is positioned on a portion of the first bone engaging feature that is constructed and arranged to be positioned close to a portion of the bone that is angled away from a vertical plane that bisects the first bone through dorsal and ventral sides of the first bone.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. Various embodiments of the invention will now be described, by way of example, with reference to the accompanying drawings, in which.

DETAILED DESCRIPTION

Hallux valgus and tailor's bunions have a wide variety of causes. Some deformities may be inherited or present at birth, while others are self-inflicted. Self-inflicted causes include high-heeled or ill-fitting shoes, high-impact exercise, foot injuries, and the like.

Figure 1B:
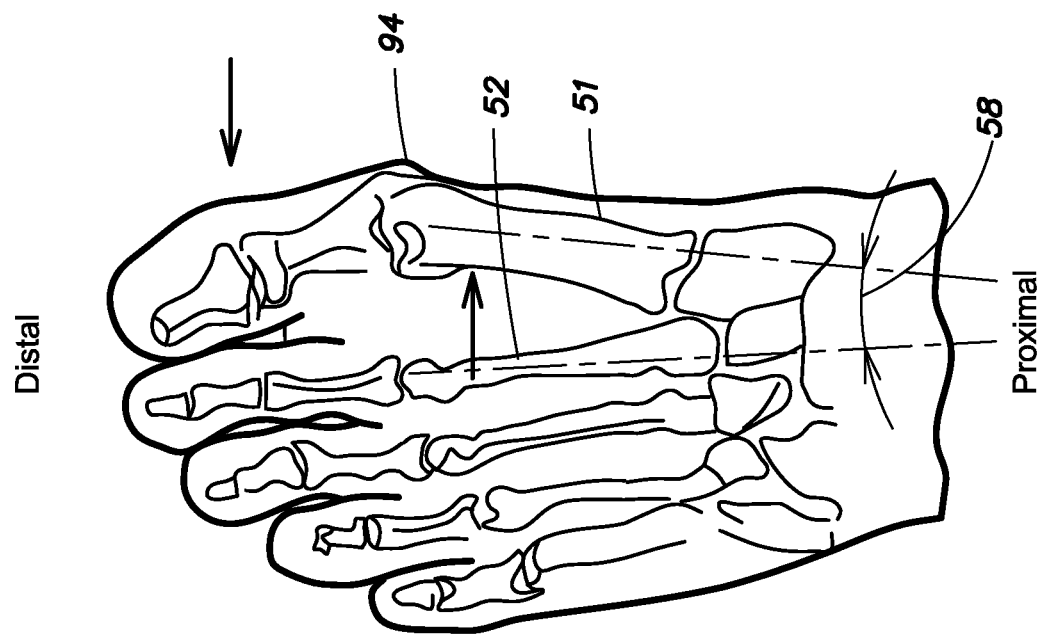
FIG. 1B depicts a foot exhibiting hallux valgus.
Figure 1A:
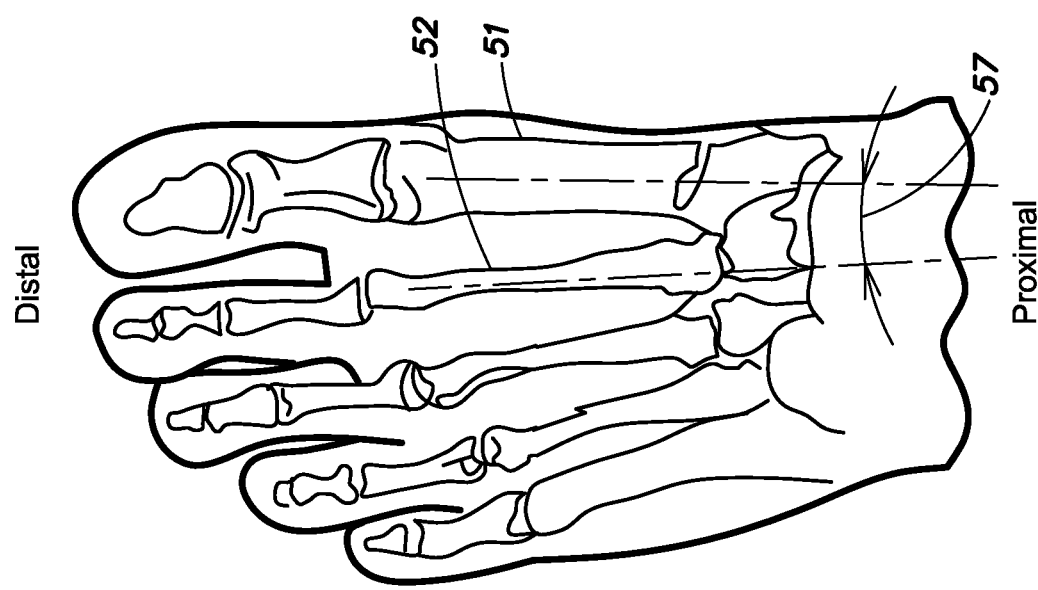
FIG. 1A depicts a healthy foot without hallux valgus.
Figure 2:
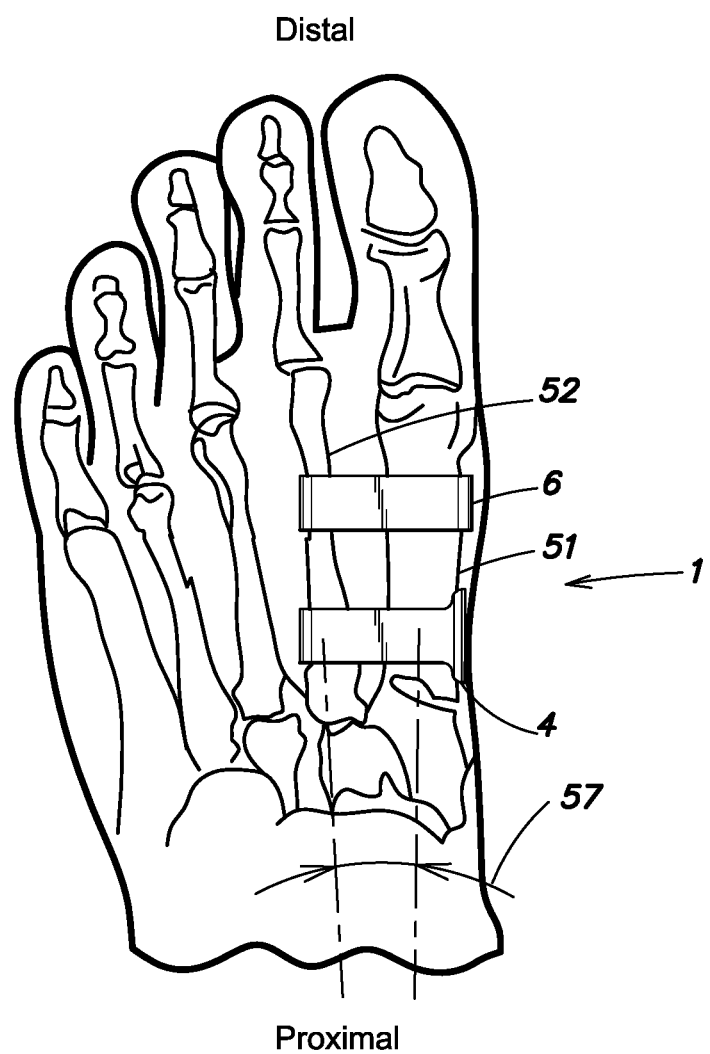
FIG. 2 depicts a corrected foot with an implant system positioned on the first and second metatarsals in accordance with an aspect of the invention.

FIG. 1A depicts a healthy foot while FIG. 1B depicts a foot exhibiting hallux valgus. Hallux valgus may develop when the pressures of bearing and shifting of weight fall unevenly on the joints and tendons in the feet. This imbalance and pressure makes the big toe joint unstable, leading to splaying of the first 51 and second 52 metatarsals, and resulting in a protrusion 94 at the MTP joint of the first metatarsal. As shown in FIG. 1A, in a normal foot, the intermetatarsal angle 57 between the first 51 and second 52 metatarsal bones is typically less than about 9 degrees. As shown in FIG. 1B, a foot exhibiting hallux valgus has an intermetatarsal angle 58 between the first 51 and second 52 metatarsal bones greater than that of a normal foot, ranging from about 9 to 20 degrees. As shown in FIG. 2, implant system 1, including proximal implant 4 and distal implant 6, may stabilize the first metatarsal 51 to the second metatarsal 52, resulting in a more anatomically correct intermetatarsal angle 57 resembling that of the healthy foot in FIG. 1A.

Figure 12B:
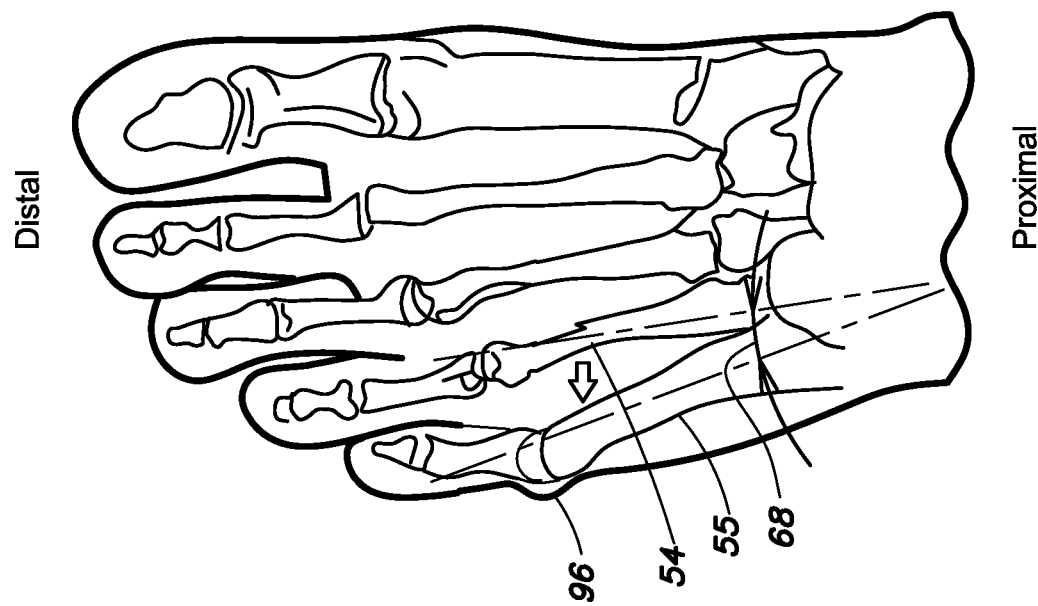
FIG. 12B depicts a foot exhibiting tailor's bunion.
Figure 12A:
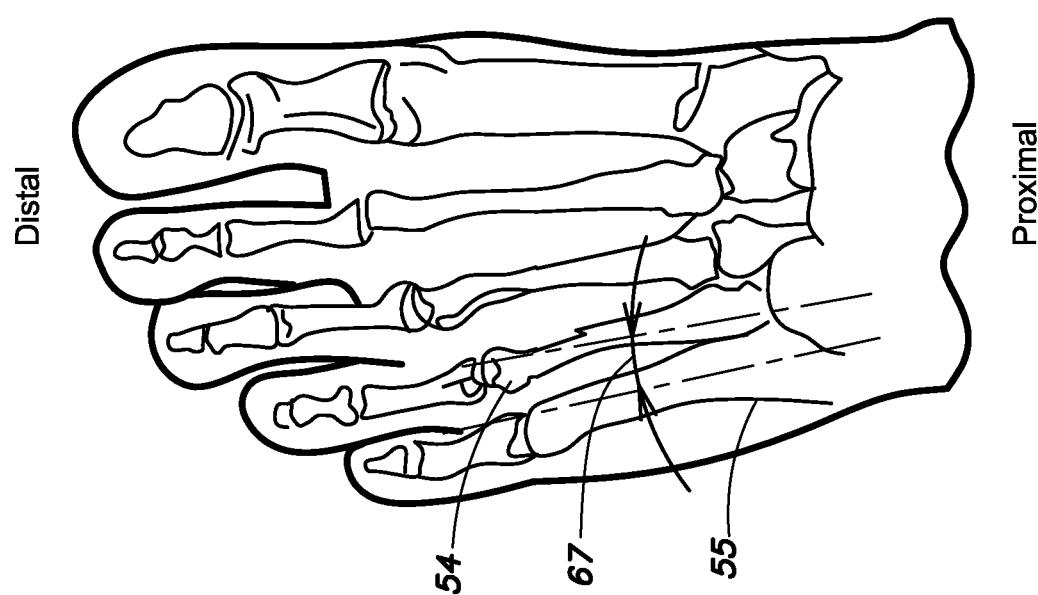
FIG. 12A depicts a healthy foot without tailor's bunion.

Similarly, tailor's bunion involves instability of the fifth metatarsal that leads to splaying of the fourth and fifth metatarsals. FIG. 12A depicts a healthy foot while FIG. 12B depicts a foot with tailor's bunion. With tailor's bunion, splaying of the fourth 54 and fifth 55 metatarsal results in a protrusion 96 at the MTP joint of the fifth metatarsal. As shown in FIG. 12A, in a normal foot, the intermetatarsal angle 67 between the fourth 54 and fifth 55 metatarsal bones is typically less than about 8 degrees. As shown in FIG. 12B, a foot with tailor's bunion has an intermetatarsal angle 68 between the fourth 54 and fifth 55 metatarsal bones greater than that of a normal foot, ranging from about 8 to 15 degrees.

One challenge with the use of surgical implants is attachment to the bones. Prior implants anchor to the foot bones by fully penetrating through the metatarsals and/or wrapping completely around the metatarsals. Arrangements that penetrate completely through the metatarsals are more invasive, as they may weaken the structural integrity of the bones and lead to stress fractures and stress risers. Arrangements that wrap completely around the metatarsals may require invasive surgical procedures, and may be bulky and uncomfortable to the patient.

According to one aspect of the invention, the surgical implant may partially wrap around the metatarsal bone rather than penetrate completely through the entire metatarsal bone, and may be positioned on only the dorsal side of the metatarsal bones, allowing the implant to engage the metatarsals while enabling a less invasive surgical procedure.

Figure 3A:
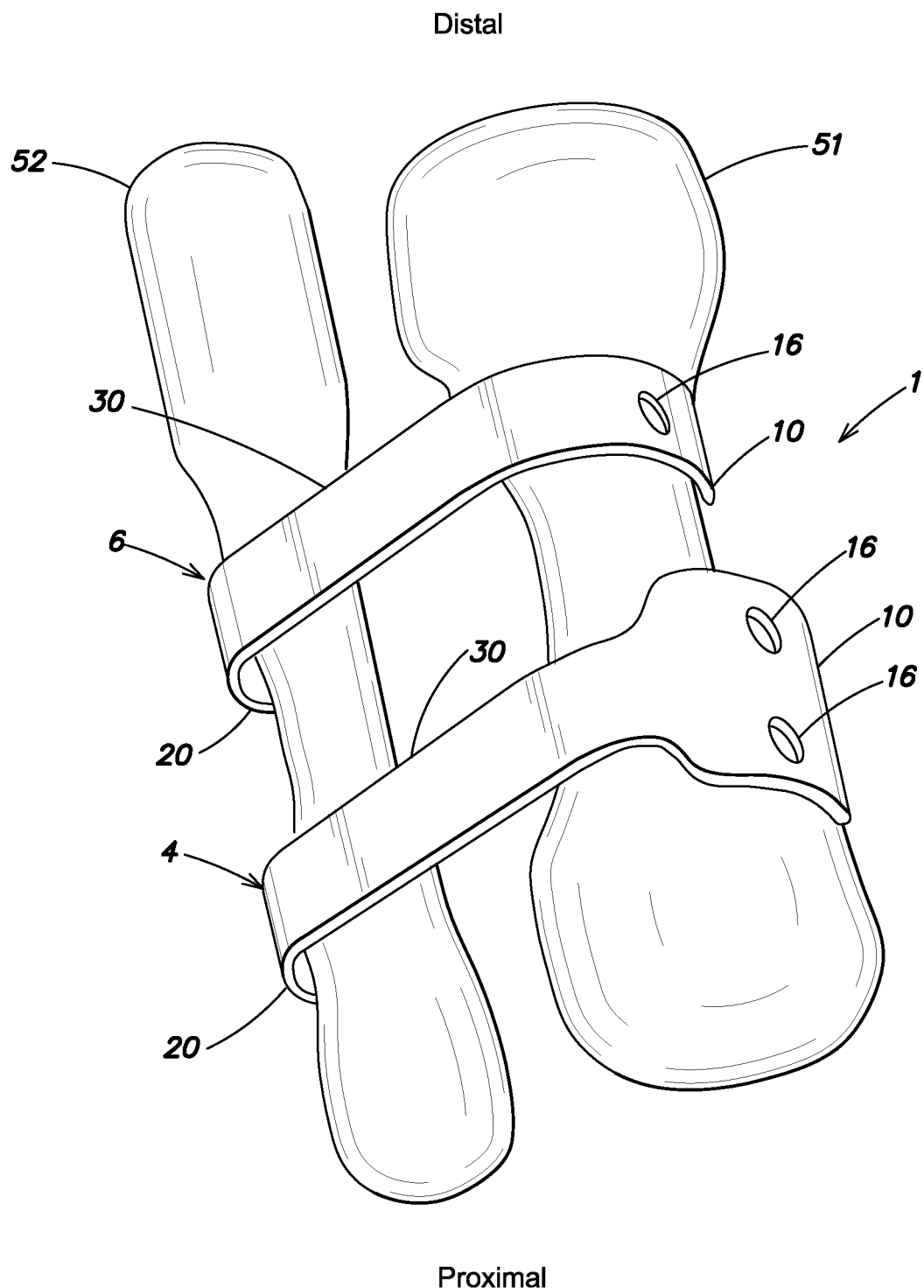
FIG. 3A depicts a top perspective view of first and second metatarsals with an implant system in accordance with an aspect of the invention.
Figure 3B:
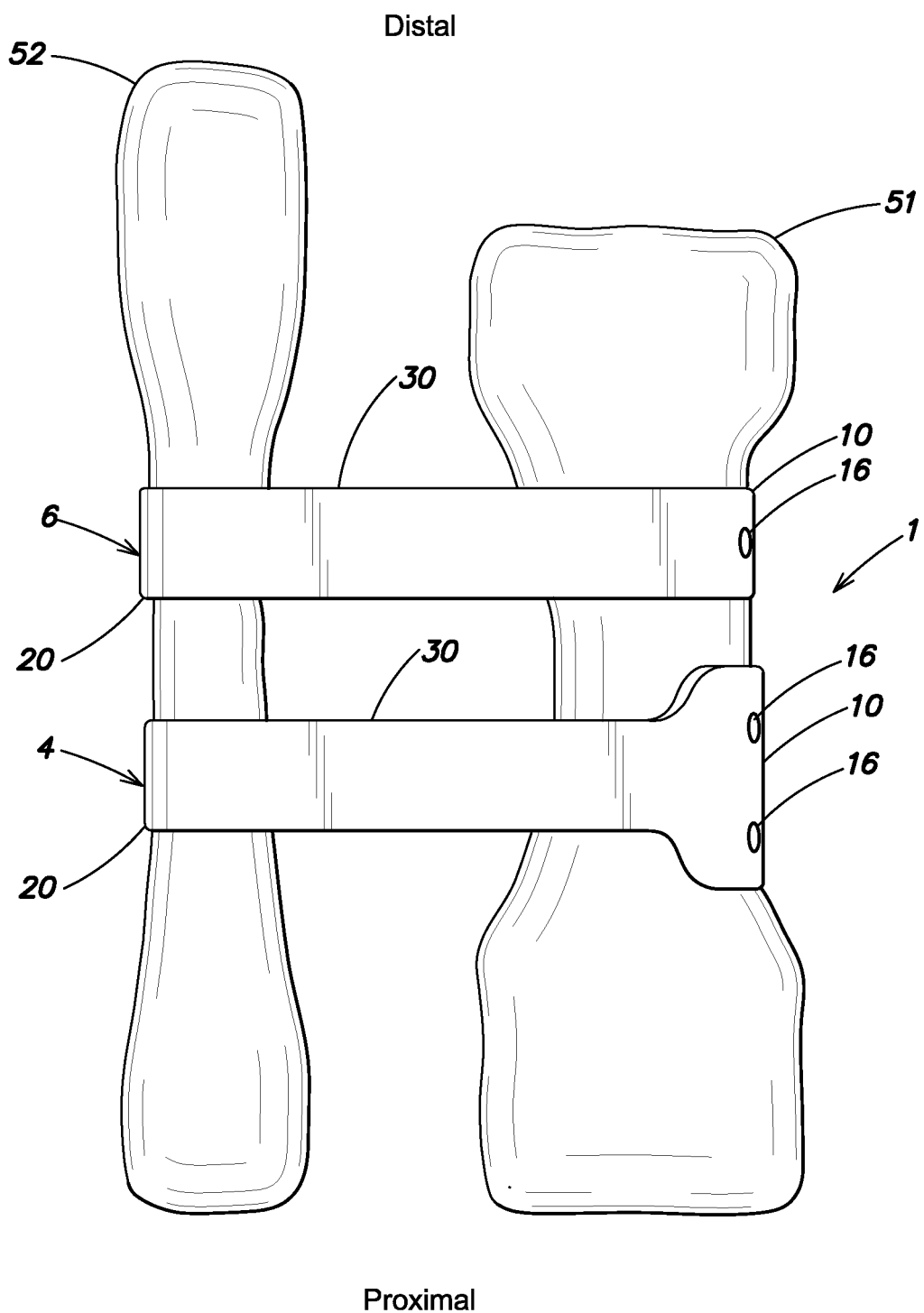
FIG. 3B depicts a top view of FIG. 3A.

According to one aspect, the implant includes one or more features enabling attachment or coupling of the implant to the bone. In this manner, the implant can exert an appropriate hold on the bone to urge it into its correct anatomical position. As shown in FIGS. 3A-B, in one embodiment, implants 4, 6 may include a first bone engaging feature 10 at one end that is constructed in a manner to engage the first metatarsal bone 51, and a second bone engaging feature 20 at the other end that is constructed in a manner to engage the second metatarsal bone 52.

Figure 5:
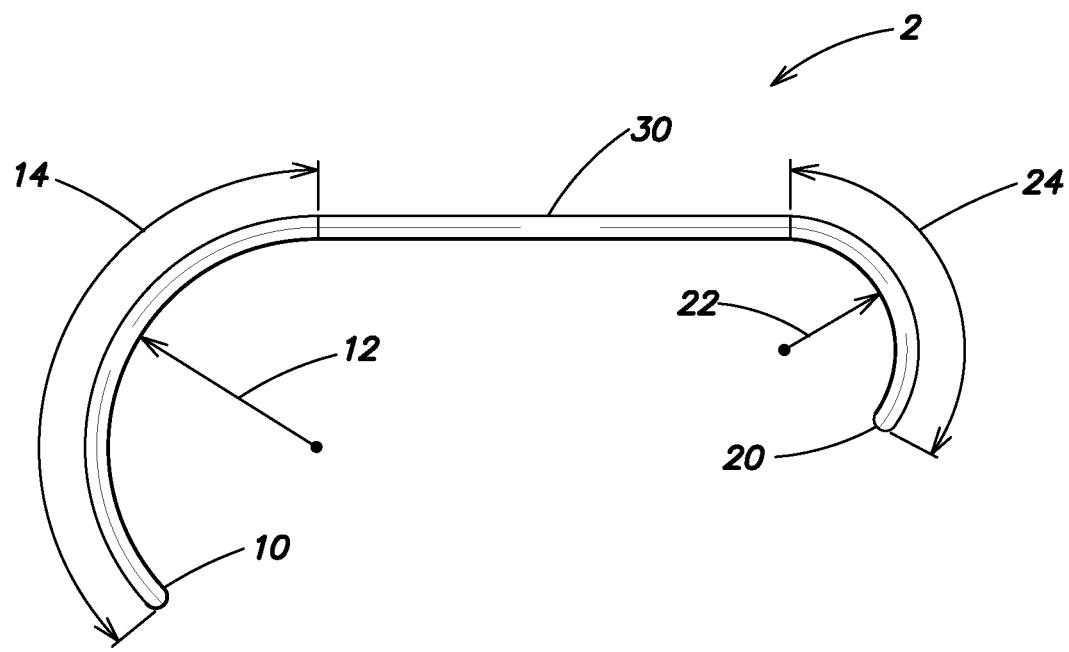
FIG. 5 depicts a side view of the implant of FIG. 4A.
Figure 6:
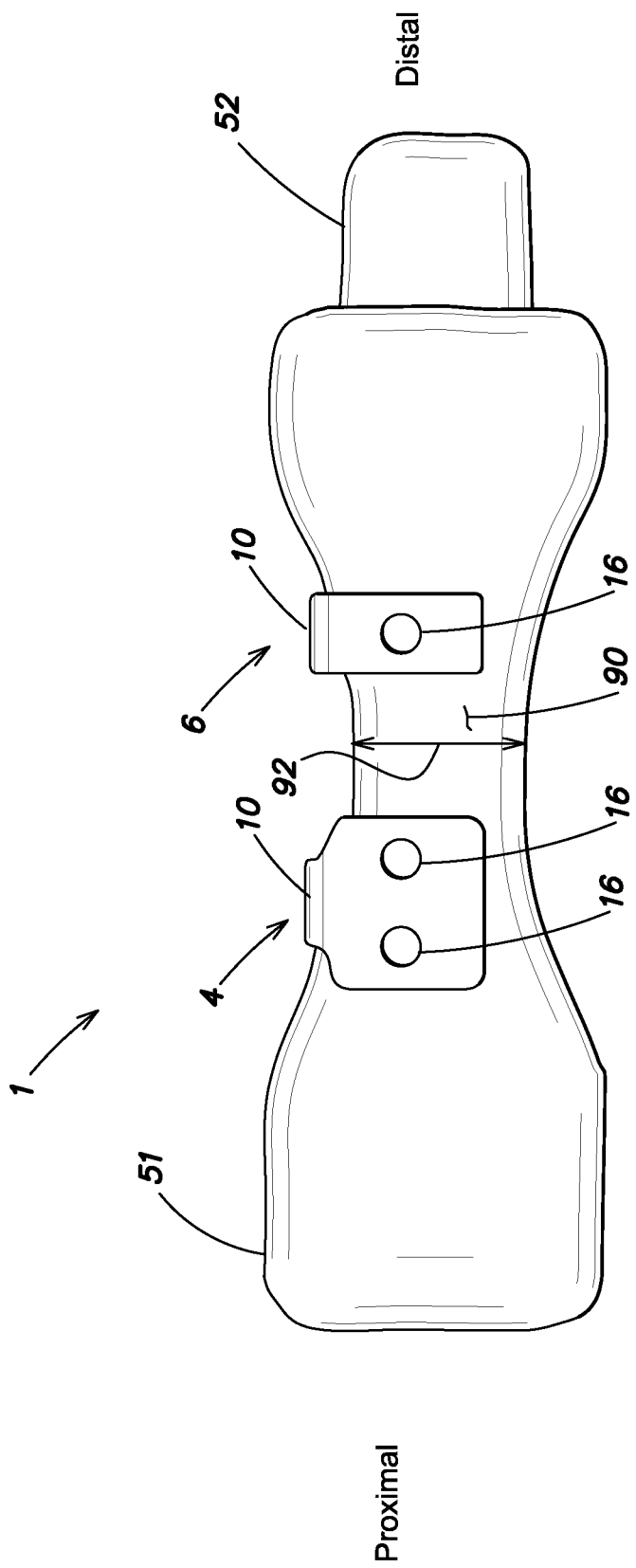
FIG. 6 depicts a medial view of FIG. 3A.
Figure 7A:
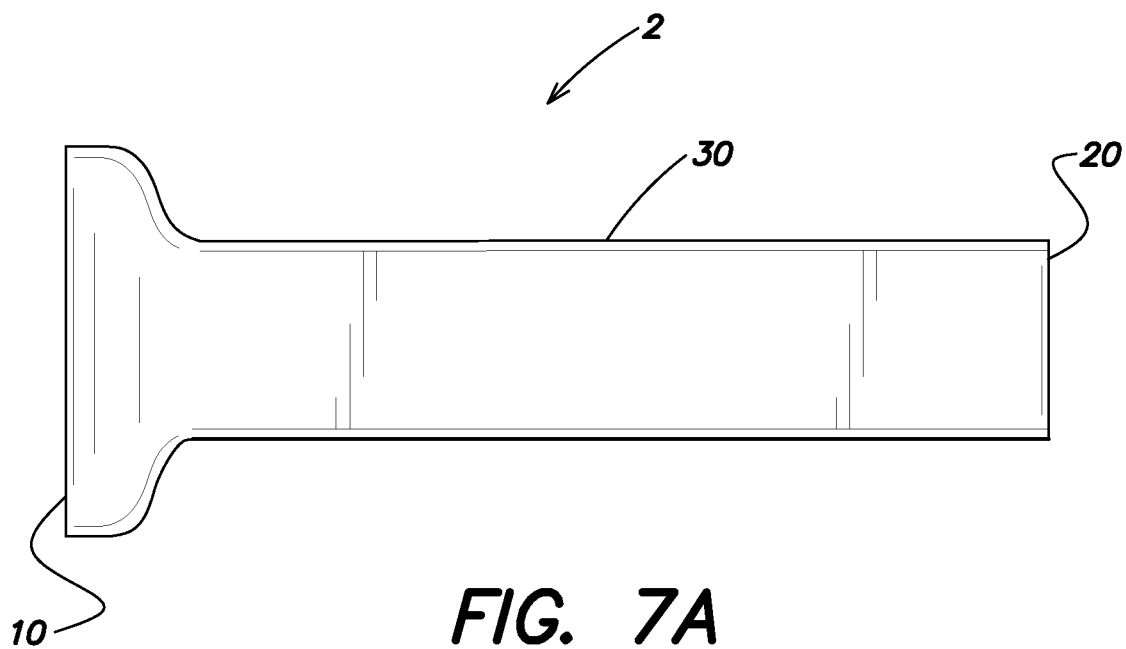
FIG. 7A depicts a top view of the implant of FIG. 4A.
Figure 7B:
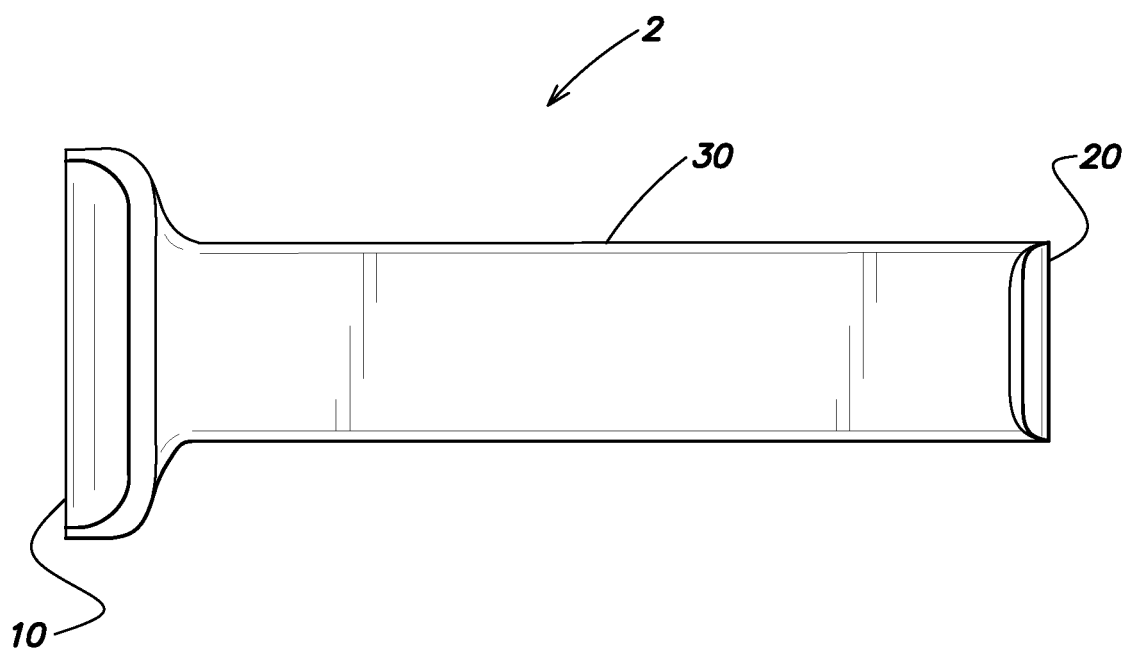
FIG. 7B depicts a bottom view of the implant of FIG. 4A.

In one embodiment, the bone engaging feature is shaped to partially wrap around the bone. In the embodiment shown in FIG. 5, the side profile of implant 2 may form a C-shape to hook on the lateral or medial aspect of a bone. Each bone engaging feature 10, 20 may have a specific radius of curvature and arc length. The radius of curvature and arc length of each bone engaging feature may allow each end of the implant to hook on the lateral or medial aspect of a bone, thereby partially wrapping around the bone. First bone engaging feature 10 has a radius of curvature 12 and arc length 14. Likewise, second bone engaging feature 20 has a radius of curvature 22 and arc length 24. The radius of curvature of each bone engaging feature may range from about 1 mm to 25 mm. The arc length of each bone engaging feature may range from about 1 mm to about 150 mm. As shown in FIG. 3A, first bone engaging feature 10 of the proximal implant 4 hooks on the medial aspect of the first metatarsal 51 and partially wraps around the first metatarsal 51. Similarly, as shown in FIG. 3B, second bone engaging feature 20 of the proximal implant 4 hooks on the lateral aspect of the second metatarsal 52 and partially wraps around the second metatarsal 52. Depending on its radius of curvature and arc length, the bone engaging feature may partially wrap around bone by extending to a certain dorsal-plantar depth along the lateral or medial aspect of the bone. In some embodiments, as shown in FIG. 6, the first bone engaging feature 10 partially wraps around the first metatarsal 51 by extending down to more than half the dorsal-plantar depth 92 of the medial aspect 90 of the first metatarsal 51. In some embodiments, a bone engaging feature may partially wrap around bone by extending to slightly more than half the dorsal-plantar depth, half the dorsal-plantar depth, slightly less than half the dorsal-plantar depth, or less than half the dorsal-plantar depth of the lateral or medial aspect of a bone. In some embodiments, the bone engaging features may also be shaped to fit the medial-lateral contours of bone. For example, a distal portion of bone engaging feature 10 may curve inward medially (not shown) to meet the first metatarsal 51. Of course, it should be appreciated that the present invention is not limited in this respect and other suitable shapes may be employed. For example, the bone engaging feature may be formed in a semi-circular shape or otherwise have a longer arc length to wrap further, but still partially, around the bone. In some cases, the bone engaging feature may be arranged to wrap completely around the bone.

According to one aspect, the bone engaging features may be configured to provide a close anatomical fit to the patient such that the distance between the implant and the metatarsals in the ventral-dorsal direction is decreased. Providing a close anatomical fit may help enhance patient comfort. A large distance between the implant and the metatarsals in the ventral-dorsal direction may give rise to a bulky protrusion on the dorsal surface of the foot which may interfere with daily activities and cause discomfort. In addition, a poorly fit implant may be more easily disturbed or dislodged by external forces on the foot. In some embodiments, the radius of curvature and arc length of the bone engaging features may be adjustable to provide a close anatomical fit to the patient. The bone engaging features may be adjusted pre-operatively or intraoperatively. A surgeon may bend (manually or with a tool such as a plate bender) each end of the implant to adjust the radius of curvature and/or arc length of the bone engaging features to fit the subject's anatomy. In some embodiments, the bone engaging features may also be adjusted to fit the medial-lateral contours of bone by bending the bone engaging features in the medial or lateral direction. In another embodiment, bone engaging features may include heat-shrinkable components. In yet another embodiment, bone engaging features may include multiple segments that can be removed or added to in order to alter the radius of curvature and/or arc length. In other embodiments, the radius of curvature and arc length may be permanent, and a surgeon may choose from a set of implants with different discrete curvatures and arc lengths to best suit the subject's anatomy.

In some embodiments, the implant may include other types of bone engaging features such as anchor holes. Anchoring elements may be passed through the anchor holes and fixed into the bone, thereby anchoring the implant to the bone. Anchoring elements include bone screws, surgical screws, orthopedic screws, barbs, and other suitable hardware, as this aspect is not limited in this regard. In addition, screws may be of the locking or non-locking type, as this aspect is not limited in this regard.

In some embodiments, the implant may include other types of or additional bone engaging features that enhances attachment of the implant to the bone. Other types of bone engaging features may include bonding or cementation that adheres the implant to the bone. Such bonding or cementation may be applied at any contacting interface between the implant and the bones. Alternatively, or in addition, the implant may include surface roughness, surface coating(s), other surface treatments or other suitable feature or material that encourages ingrowth of tissue into the implant.

Figure 9:
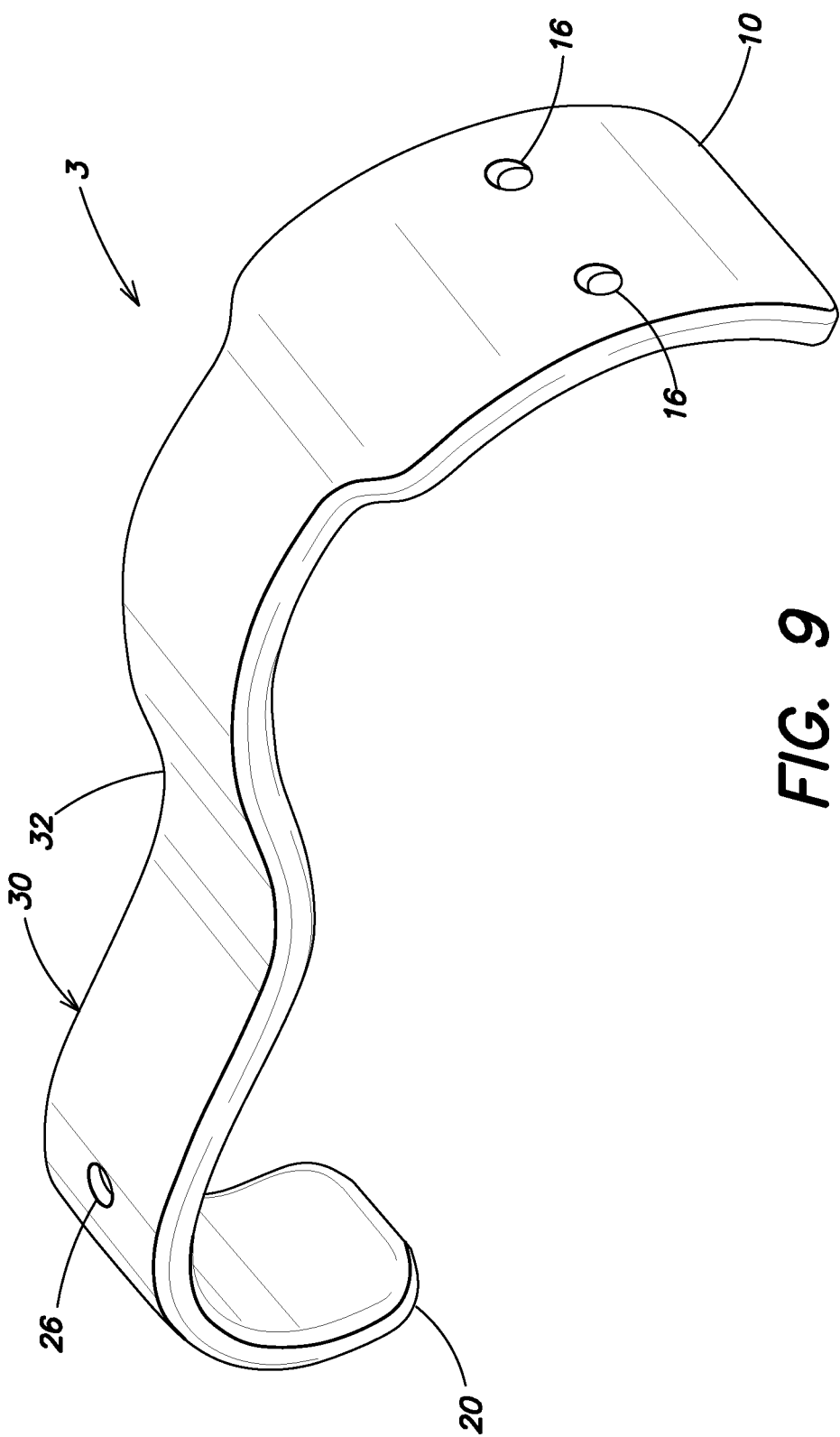
FIG. 9 depicts one embodiment of an implant including a curvature on the intermediate portion.

Bone engaging features disclosed in the above mentioned embodiments may be combined or separated, as the invention is not limited in this regard. For example, FIGS. 3A-3B illustrate an embodiment in which bone engaging features 10, 20 include a rounded shape that permits the end of the implant to wrap around the bone, combined with bone anchor holes 16, which also promote engagement between the implant to bone. Bone anchor holes may be positioned anywhere along the implant. As illustrated in FIG. 9, in some embodiments, an implant 3 may have an intermediate portion 30 that includes a dorsal bone anchor hole 26.

Figure 10:
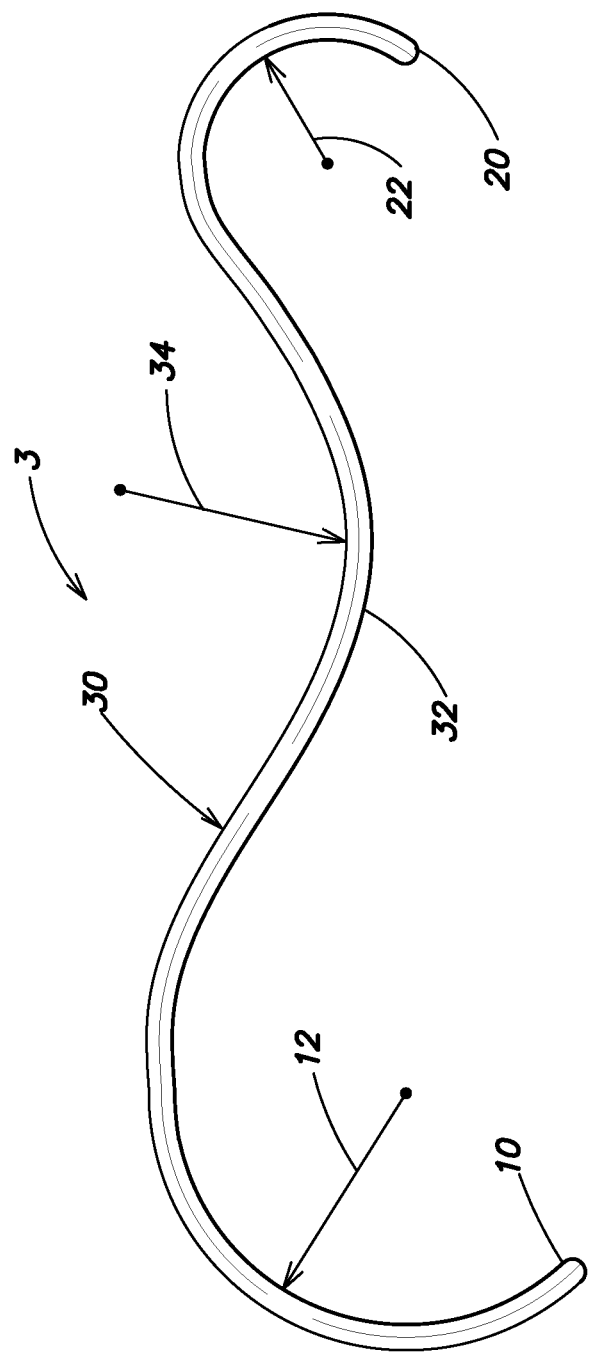
FIG. 10 depicts a side view of the implant of FIG. 9.
Figure 11A:
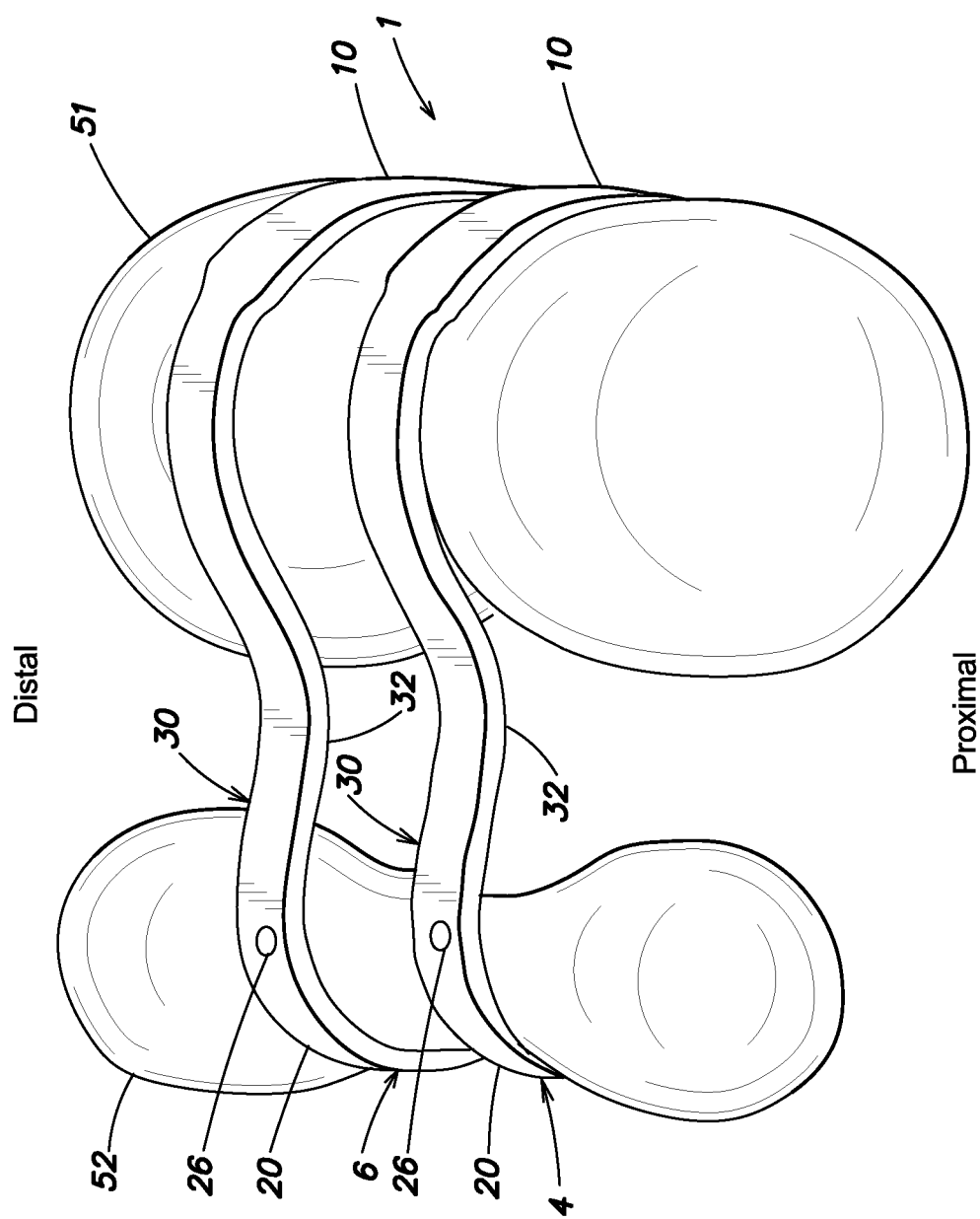
FIG. 11A depicts a top perspective view of first and second metatarsals with an implant system in accordance with an aspect of the invention.
Figure 11B:
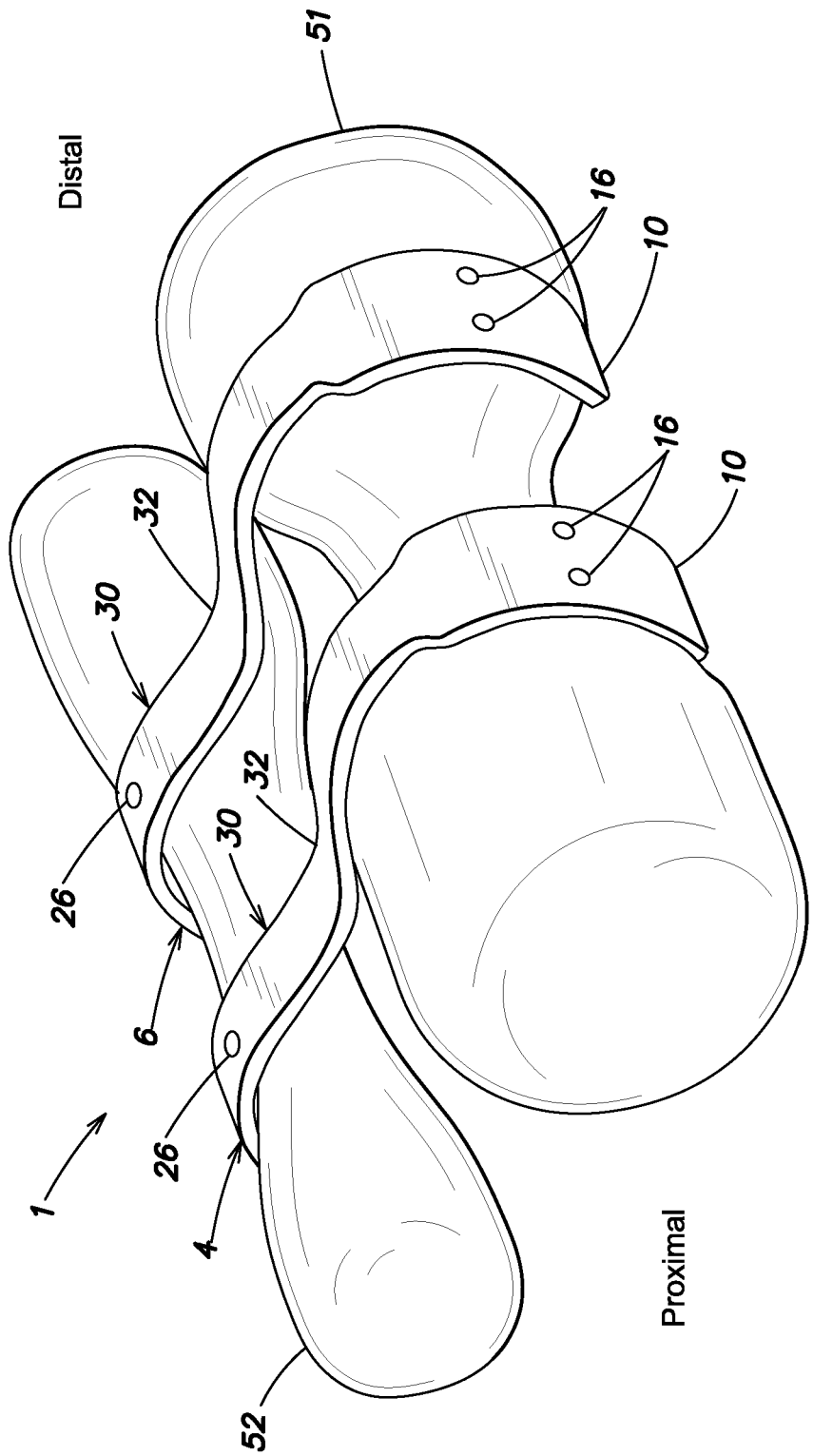
FIG. 11B depicts another top perspective view of FIG. 11A.

As can be appreciated, the implant exerts an appropriate tension force between the metatarsals to draw the first toward the second metatarsal, urging the improperly positioned metatarsal back toward its correct anatomical position. In one embodiment, as shown in FIGS. 4A-B and 7A-B, the implant includes an intermediate portion 30 connecting the first 10 and second 20 bone engaging features. In some embodiments, the intermediate portion connects only a first bone engaging feature and a second bone engaging feature such that the implant is constructed and arranged to only couple to two bones. In this particular embodiment, the intermediate portion has a substantially flat profile. In some embodiments, in order to improve the anatomical fit of the implant, the intermediate portion may include a curvature. As shown in FIGS. 9-10, intermediate portion 30 of implant 3 includes a curvature 32. The curvature may be positioned such that, when the implant is engaged with the metatarsals, the curvature is positioned between the metatarsals. This curvature may allow the implant to be positioned closer to the metatarsals in the ventral-dorsal direction, thereby reducing the ventral-dorsal distance from the implant to the bones. FIGS. 11A-B depict one embodiment in which intermediate portion 30 includes a curvature 32 positioned between the first 51 and second 52 metatarsals.

Figure 4A:
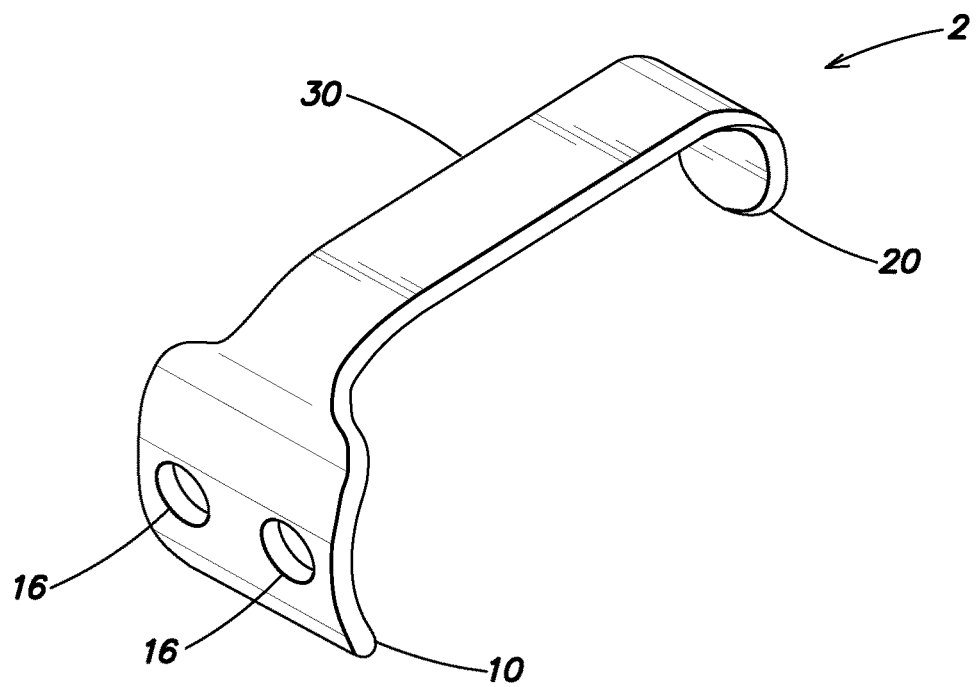
FIG. 4A depicts a top perspective view of one embodiment of an implant.
Figure 4B:
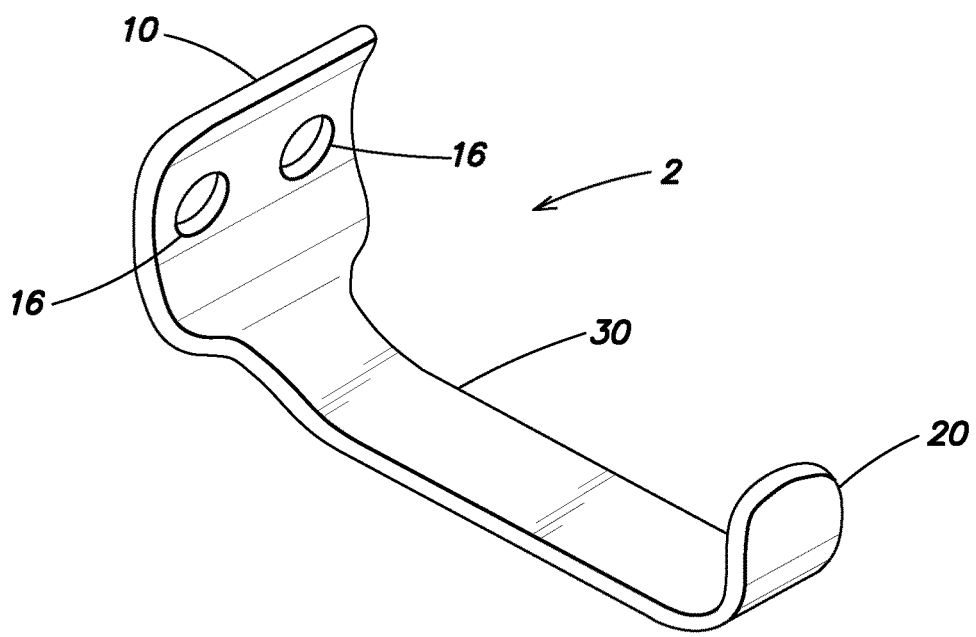
FIG. 4B depicts an underside perspective view of the implant of FIG. 4A.
Figure 4C:
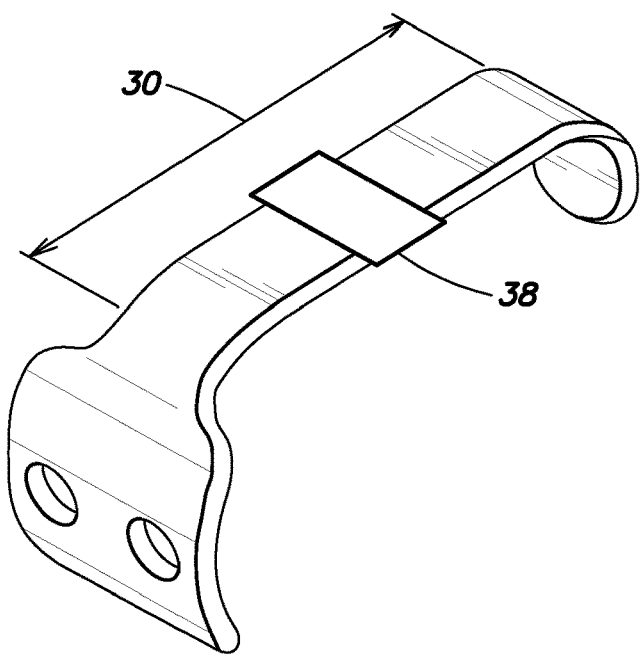
FIG. 4C depicts an implant with an adjustable section.
Figure 4D:
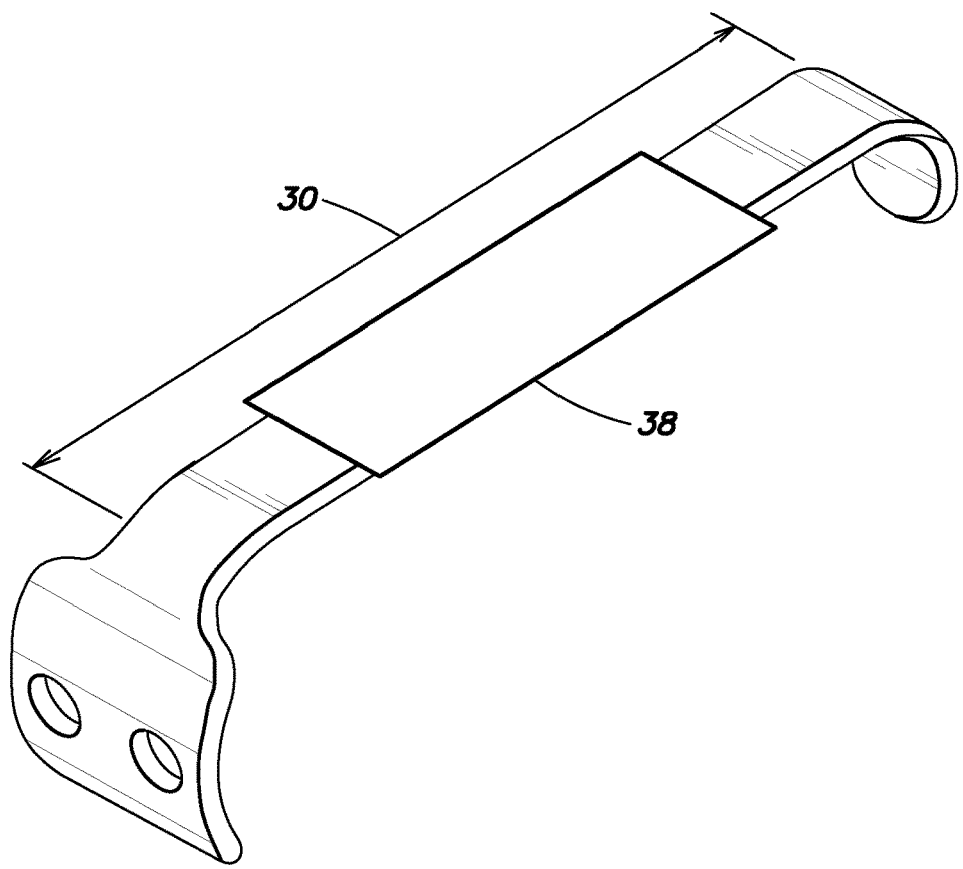
FIG. 4D depicts the implant of FIG. 4C with an expanded adjustable section.

According to one aspect, the intermediate portion may be adjustable to enhance the anatomical fit of the implant. In some embodiments, the intermediate portion may have an adjustable length, width, and/or curvature. For example, the intermediate portion may include heat shrinkable components, slidably adjustable components, and/or bendable components that permit a user to adjust the length, width, and/or curvature of the intermediate portion. For example, FIGS. 4C-D shows schematics of an implant with an adjustable section 38 that expands from a shorter length in FIG. 4C to a longer length in FIG. 4D, thereby increasing the overall length of the intermediate portion 30. In one embodiment, the adjustable section may include one or more struts that may be length-adjustable, such as a turnbuckle-like device. In another embodiment, the adjustable section may include multiple telescoping segments such that the intermediate portion can be expanded or compressed to various lengths. In yet another embodiment, adjustable section may include multiple removable segments. Segments may be added or removed to increase or decrease the length of the adjustable section. In another embodiment, the adjustable section may include two segments that can be interlocked with one another at multiple positions to enable a range of intermediate portion lengths. For example, the first segment may have a series of slots arranged linearly along the length of the first segment. The second segment may have a series of tabs arranged linearly along the length of the second segment. The tabs on the second segment may be sized to be able to slide into the slots on the first segment. The tabs and slots may be arranged such that engagement between the tabs and slots locks the tabs in place, e.g., by shaping tabs into a hooked configuration that can hook onto the slots, by interference fit between the tabs and the slots, or by other suitable arrangement. The length of the intermediate portion is adjusted by sliding the two portions relative to one another and changing the amount of overlap between the two portions. A maximum amount of overlap between the two portions enables a minimum intermediate portion length, while a minimum amount of overlap between the two portions enables a maximum intermediate portion length. The adjustable section may span the entire length and width of the intermediate portion, or the adjustable section may be only one section of the intermediate portion. In addition, the intermediate portion may be bendable, either by hand or with a tool such as a plate bender, to create a curvature suitable to the patient's anatomy. The intermediate portion may be adjusted preoperatively or intraoperatively.

According to one aspect, the intermediate portion may be located on only one side of the bone. In some embodiments, where the implant is used in a foot, the intermediate portion may be located only dorsal to the metatarsals, such that the intermediate portion is positioned above the metatarsals, as opposed to between the metatarsals or below the metatarsals. Such an arrangement may provide increased patient comfort and may require a less invasive implantation procedure.

Figure 11C:
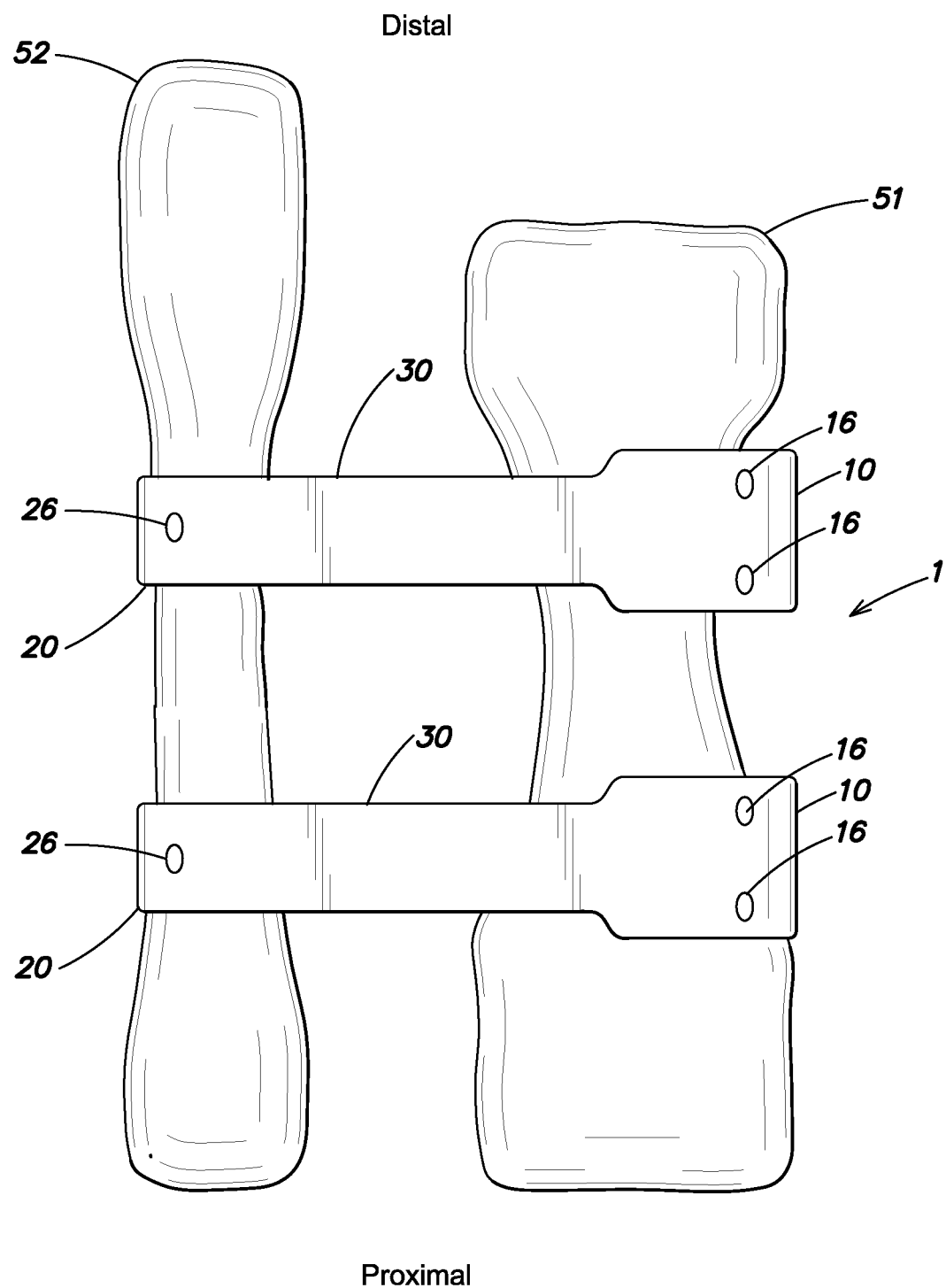
FIG. 11C depicts a top view of FIG. 11A.

According to another aspect, the intermediate portion may contact bone. In some embodiments, the intermediate portion may contact the dorsal aspect of the metatarsals. In some embodiments, the intermediate portion may include at least one bone anchor hole arranged to accept an anchoring element that anchors the implant to the bone. As shown in FIGS. 11A-C, dorsal bone anchor hole 26 is arranged to accept an anchoring element that anchors the implant to the dorsal aspect of the second metatarsal 52. In some embodiments, the intermediate portion may include surface roughness or other suitable feature that encourages ingrowth of tissue into the intermediate portion to help hold the implant in place.

Figure 8:
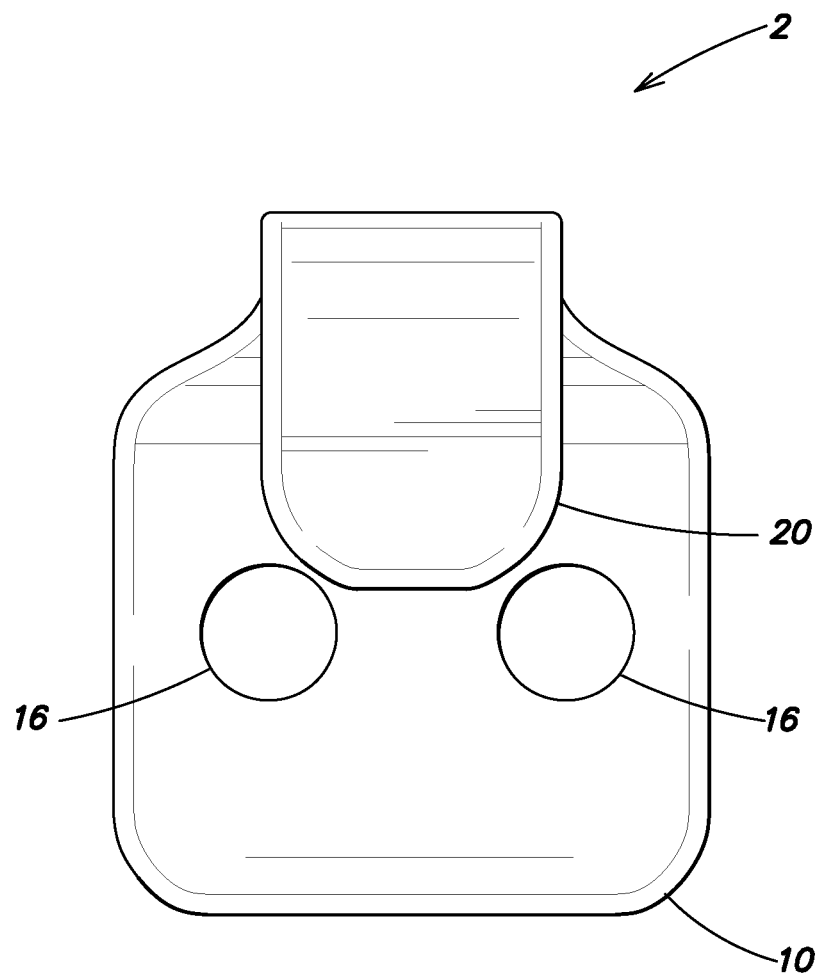
FIG. 8 depicts a lateral view of the implant of FIG. 4A.

According to one aspect, the width of the implant in the distal-proximal direction is configured to provide a sufficient surface area of contact between the implant and the bone. A larger surface area of contact may permit the implant to better attach to the bone. In some instances, a wider distal-proximal width may permit an increased number of anchoring elements to fit on the implant. On the other hand, the width of the implant may be limited by the anatomy of the patient and by considerations of invasiveness and comfort. For example, wider implants may require more extensive incisions during implantation and may hinder movement of the foot. Arrangements may be selected depending on the patient's anatomy. For example, if there is sufficient surface area on the bone at the implantation site, an enlarged bone engaging feature may be used. In some embodiments, the width of the implant in the distal-proximal direction may be uniform. For example, as shown in FIGS. 3A-B, distal implant 6 has a constant distal-proximal width throughout the entire length of the device. The first bone engaging feature 10, second bone engaging feature 20, and intermediate portion 30 of distal implant 6 all have the same width. In other embodiments, the distal-proximal width of the implant may be non-uniform. For example, as shown in FIGS. 3A-B, proximal implant 4 has an enlarged first bone engaging feature 10, such that the distal-proximal width at the first bone engaging feature 10 is wider than the intermediate portion 30 and the second bone engaging feature 20. Similarly, in FIGS. 7-8, implant 2 has an enlarged first bone engaging feature 10 such that the distal-proximal width at the first bone engaging feature 10 is wider than the intermediate portion 30 and the second bone engaging feature 20. In addition, FIGS. 3A-B also show that the distal-proximal width of proximal implant 4 steps down from a wider width at first bone engaging feature 10 to a more narrow width that is uniform from the intermediate portion 30 to the second bone engaging feature 20. Of course, it should be appreciated that the present invention is not limited in this respect and other arrangements may be employed. In one embodiment, the proximal implant may have a constant distal-proximal width, while the distal implant may have an enlarged first and/or second bone engaging feature. In another embodiment, the distal implant may have a constant distal-proximal width, while the distal implant may have an enlarged first and/or second bone engaging feature. In another embodiment, the distal and proximal implants may both have constant distal-proximal widths. In yet another embodiment, the distal and proximal implants may both have enlarged first and/or second bone engaging features. In yet another embodiment, the first bone engaging feature, the second bone engaging feature, and the intermediate portion may all have different distal-proximal widths from one another.

The implant is implanted into the body of a patient according to various aspects of the invention. In the case of treating hallux valgus or tailor's bunion, a surgical procedure is required for implantation of the implant. Prior to surgery, images may be taken of the implantation site and anatomical measurements may be made. Images may include X-Rays, Magnetic Resonance Imaging (MRI), Computed Tomography (CT) scans, or other suitable images. Anatomical measurements may include the intermetatarsal angle (the interior angle between the first and second metatarsals for hallux valgus or the interior angle between the fourth and fifth metatarsals for tailor's bunion), the distance between the first and second metatarsophalangeal (MTP) joints for hallux valgus (fourth and fifth MTP joints for tailor's bunion), curvature of the metatarsals, etc. Based on the images and anatomical measurements, a suitable-sized implant is chosen. Depending on the anatomy of the patient, the implant may be used as a proximal implant or a distal implant. As shown in FIGS. 3A-B, an implant system 1 may include both a proximal implant 4 and a distal implant 6.

In some embodiments, an implant system composed of multiple implants may be used. In some cases, the use of multiple implants may depend on the patient's intermetatarsal angle. In general, a normal intermetatarsal angle is less than about 9 degrees. In some embodiments, if the subject's intermetatarsal angle is less than about 12 degrees, a single implant may be sufficient. In some embodiments, if the subject's intermetatarsal angle is over about 12 degrees, two implants may be used. As shown in FIGS. 2, 3, and 11, a first implant 4 may be implanted at a proximal location and a second implant 6 may be implanted at a distal location. Of course, it should be appreciated that the present invention is not limited in this respect and other implantation positions may be used. For example, the first and second implants may be implanted closer or further away from each other. First implant 4 may sit at a position more or less proximally than that shown in FIGS. 3A-B, and the second implant 6 may sit at a position more or less distally than that shown in FIGS. 3A-B.

According to one aspect, first and second implants may be connected together to form a double-construct implant. For example, the double-construct implant may include a connector or section that joins first and second implants together. The connector may be arranged to be positioned in the space between the metatarsals upon implantation such that the double-construct implant forms an H-shape configuration. Alternatively, in some embodiments, the connector joining the first and second implants may be a plate that is wider than the space between the metatarsals. In another embodiment, the double-construct implant may have multiple connectors that join the first and second implants together. First and second implants may be connected together in any suitable way to form a double-construct implant, as this aspect is not limited in this regard. In some embodiments, the connector or connectors may be adjustable to enhance the anatomical fit of the implant. In some embodiments, the connector may have an adjustable length and/or thickness. For example, the connector may include heat shrinkable components, slidably or rotatably adjustable components, and/or bendable components that permit a user to adjust the length, width, and/or curvature of the connector. In another embodiment, the connector may include multiple removable segments. Segments may be added or removed to increase or decrease the length of the connector. In addition, the connector may be bendable, either by hand or with a tool such as a plate bender, to create a curvature suitable to the patient's anatomy. The connector may be adjusted preoperatively or intraoperatively.

Figure 13:
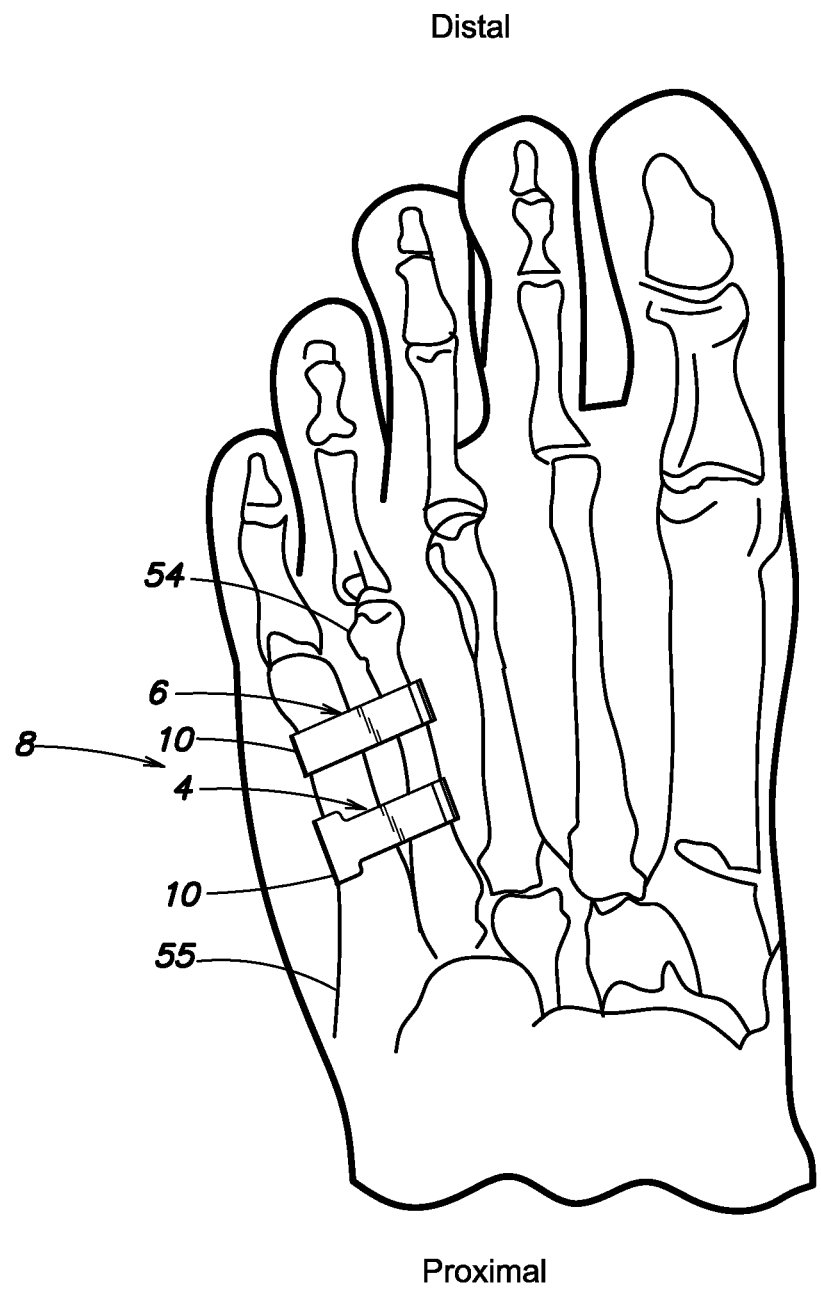
FIG. 13 depicts a corrected foot with an implant system positioned on the fourth and fifth metatarsals in accordance with an aspect of the invention.

According to one aspect, the implant is not limited to use with the first and second metatarsals. In some embodiments, the implant may be used to treat a condition called tailor's bunion, also known as a bunionette. As shown in FIG. 13, implant system 8, including proximal implant 4 and distal implant 6, may stabilize the fifth metatarsal 55 to the fourth metatarsal 54 in the same manner that the first metatarsal 51 is stabilized to the second metatarsal 52 in the treatment of hallux valgus (FIGS. 2-3). Although FIG. 13 depicts a proximal implant 4 with an enlarged first bone engaging feature 10, and a distal implant 6 with a uniform proximal-distal width, it should be appreciated that this aspect is not limited in this regard. In one embodiment, proximal implant 4 may have a uniform proximal-distal width, and distal implant 6 may have an enlarged first and/or second bone engaging feature. In another embodiment, distal implant 6 may have a uniform proximal-distal width, and proximal implant 4 may have an enlarged first and/or second bone engaging feature. In yet another embodiment, both implants 4, 6 may have uniform proximal-distal widths. In other embodiments, a single implant or a double-construct implant may be used. Any arrangement suitable to fit the patient's anatomy may be used, as this aspect is not limited in this regard.

According to one aspect, the implant may include one or more flexure features that permit the metatarsals that are engaged by the implant to move relative to one another after the implant has been implanted. As a result, even with the implant implanted inside the patient's foot, the metatarsals of the patient's foot may have some degree of freedom to move relative to one another. In some cases, permitting relative movement between the engaged metatarsals may provide any one or combination of the following: improve comfort, decrease mechanical stresses or other wear on the implant, decrease mechanical stresses or other wear on the biological tissue surrounding the implant, improve the longevity of the implant or decrease the probability of postoperative complications. In some embodiments, the implant may include one or more flexure features that permit relative movement between the engaged metatarsals in the dorsal-plantar direction. Alternatively or in addition, the one or more flexure features may permit movement between the engaged metatarsals in the lateral-medial direction. The implant may also permit the engaged metatarsals to rotate relative to one another about one or more flexure axes. The flexure feature can be any suitable arrangement that permits relative movement between the engaged metatarsals in the dorsal-plantar direction and/or the lateral-medial direction.

Figure 14A:
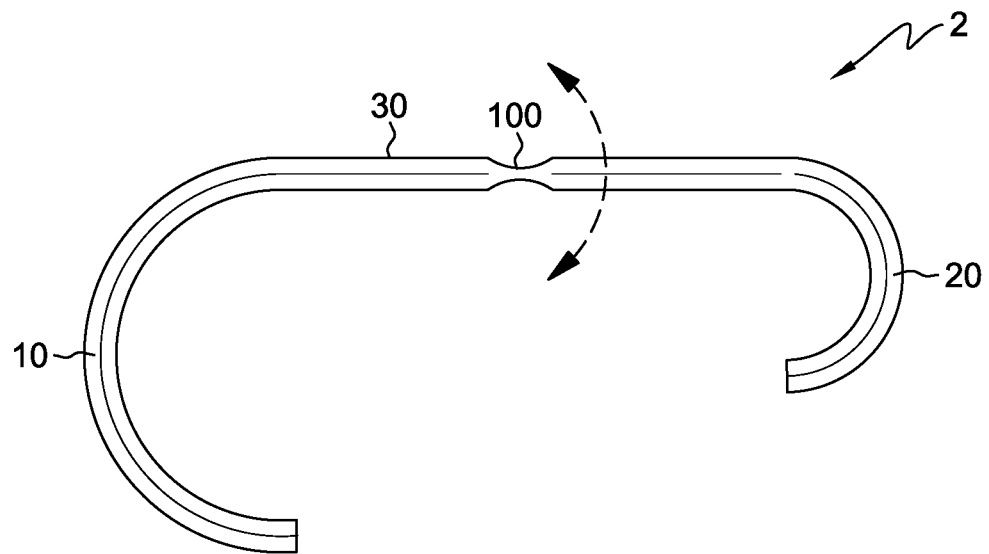
FIG. 14A depicts one embodiment of an implant including a flexure feature in accordance with an aspect of the invention.
Figure 14B:
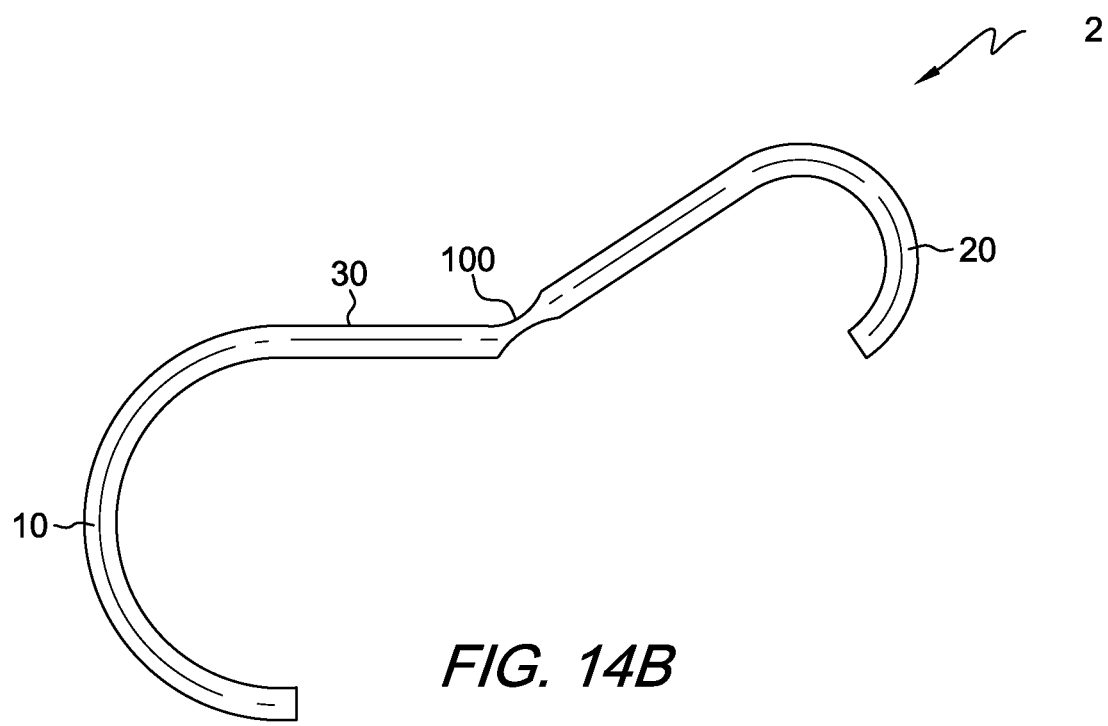
FIG. 14B depicts relative movement of first and second bone engaging features of the implant of FIG. 14A.
Figure 15:
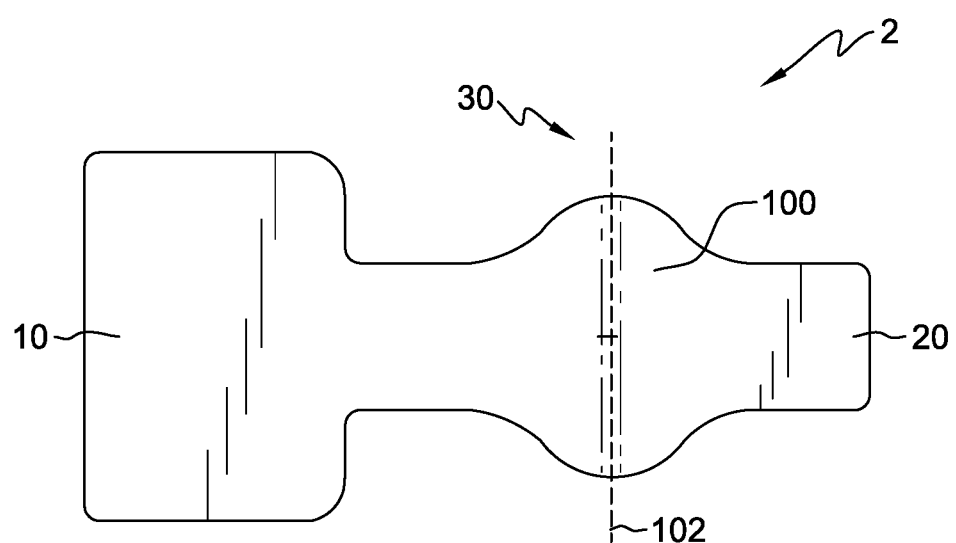
FIG. 15 depicts a top down view of the implant of FIGS. 14A and 14B.
Figure 16:
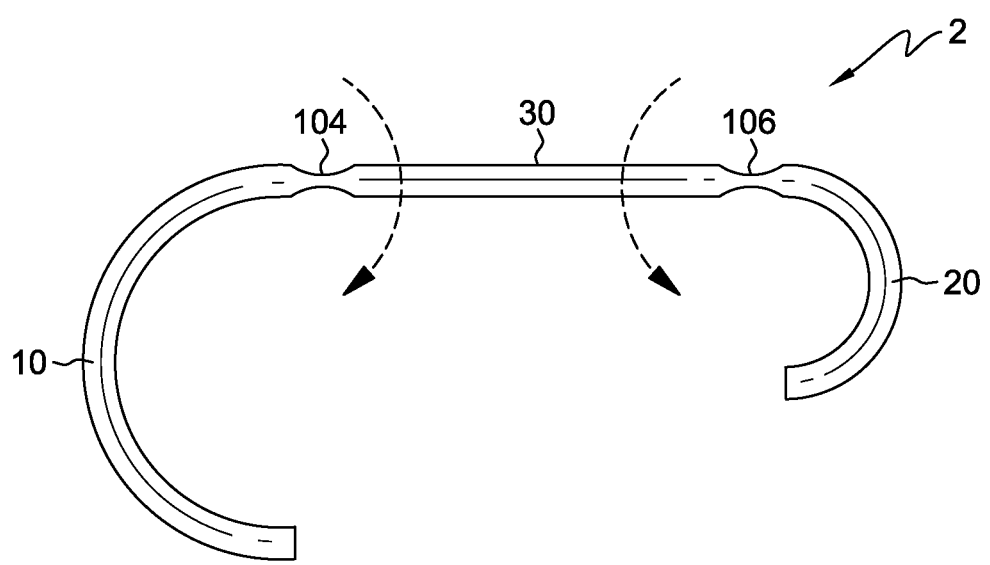
FIG. 16 depicts another embodiment of an implant including two flexure features in accordance with an aspect of the invention.
Figure 17A:
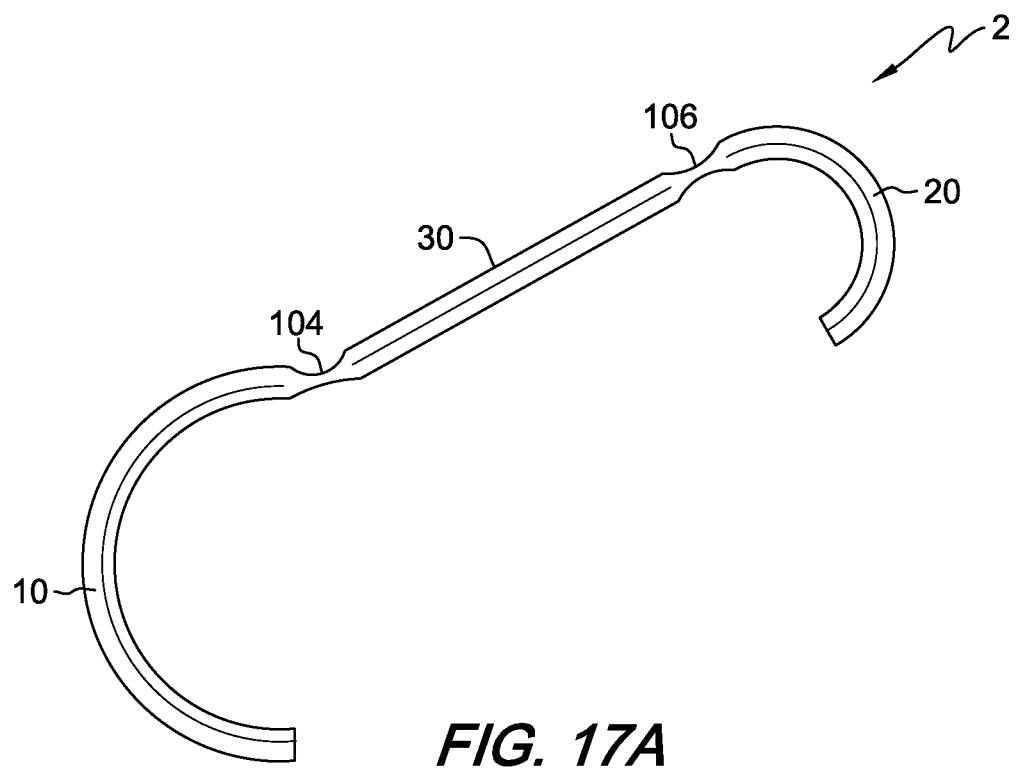
FIG. 17A depicts the implant of FIG. 16 in a first mode of operation.
Figure 17B:
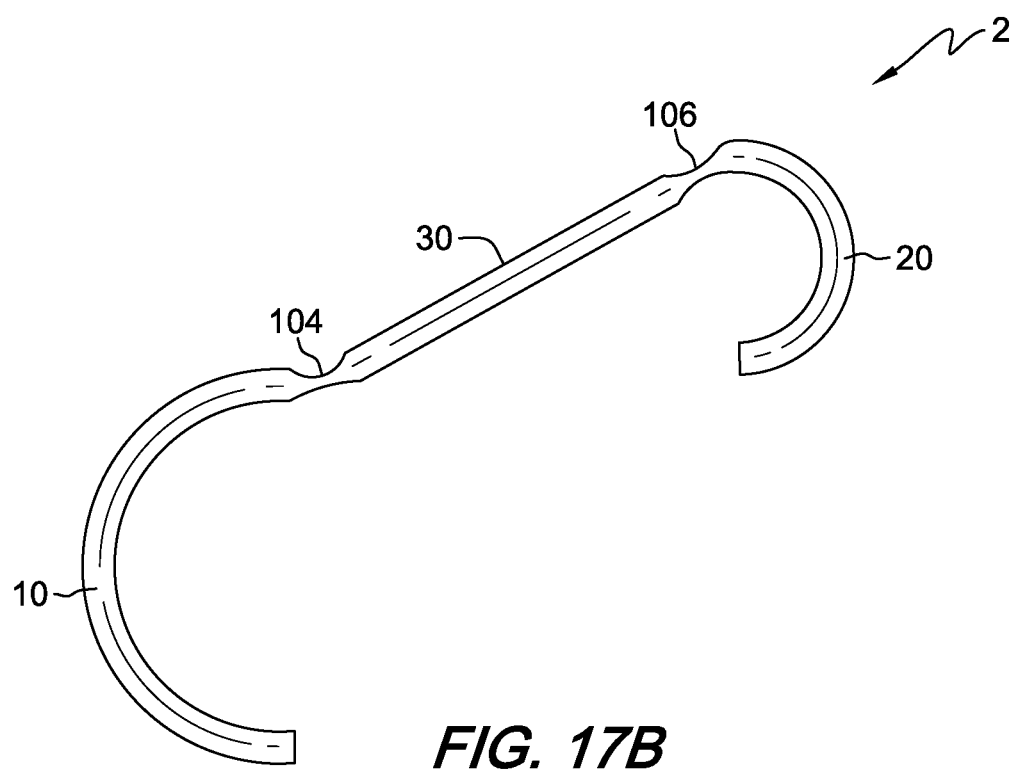
FIG. 17B depicts the implant of FIG. 16 in a second mode of operation.

In some embodiments, the flexure feature includes a region of decreased depth in the dorsal-plantar direction relative to the rest of the intermediate portion and/or the rest of the implant. The decreased depth of the flexure feature in the dorsal-plantar facilitates flexing of the implant at the flexure feature. For example, in one embodiment, shown in FIGS. 14A-14B, the intermediate portion 30 of implant 2 includes a flexure feature 100, which is a region of decreased depth in the dorsal-plantar direction relative to the rest of the intermediate portion 30. As depicted in FIG. 14B, flexure feature 100 permits bone engaging features 10 and 20 to rotate relative to one another. In another embodiment, shown in FIGS. 16-17B, the intermediate portion 30 of implant 2 includes two flexure features 104 and 106, which are regions of decreased depth in the dorsal-plantar direction relative to the rest of the intermediate portion 30. As depicted in FIG. 17B, flexure features 104, 106 permit bone engaging features 10 and 20 to rotate and translate relative to one another. To compensate for the decreased depth of the flexure feature in the dorsal-plantar direction, in some embodiments, the flexure feature has a wider width in the distal-proximal direction compared to the rest of the intermediate portion. FIG. 15 is a top down view of an implant 2 showing a flexure axis 102 of a flexure feature, about which the first bone engaging feature 10 can rotate relative to the second bone engaging feature 20. As seen in FIG. 15, flexure feature 100 has a wider distal-proximal width than the rest of intermediate portion 30. Without wishing to be bound by any theory, such an increased distal-proximal width may increase the cross-sectional area at the flexure feature and decrease the likelihood of fracture or other mechanical failure at the flexure feature 100. In other embodiments, however, the flexure feature may have the same or narrower distal-proximal width than the rest of the intermediate portion.

Figure 18A:
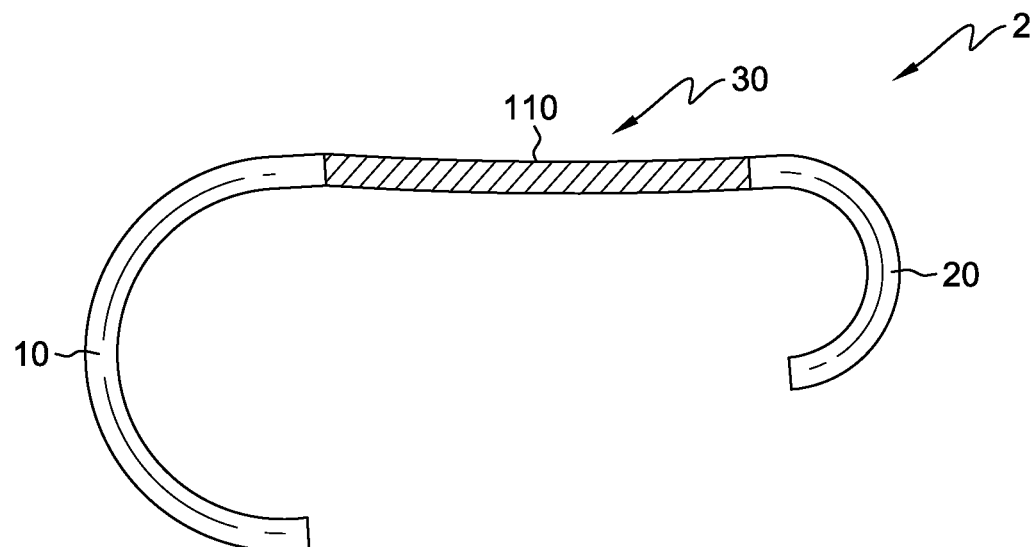
FIG. 18A depicts another embodiment of an implant including a flexure feature.
Figure 18B:
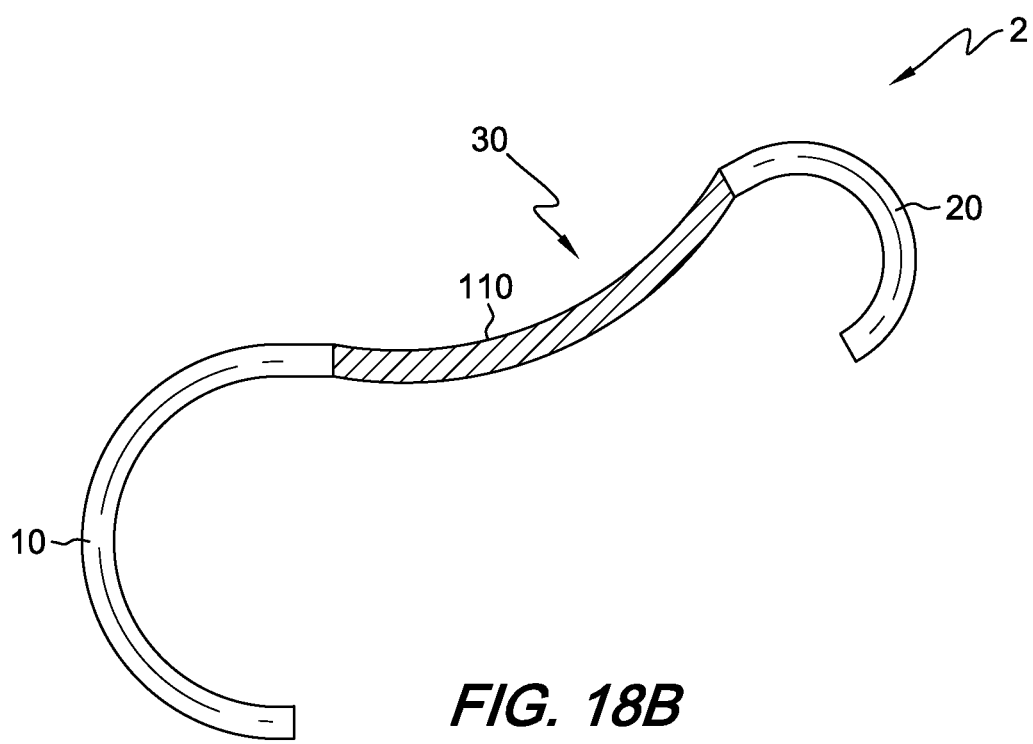
FIG. 18B depicts relative movement of first and second bone engaging features of the implant of FIG. 18A.
Figure 19A:
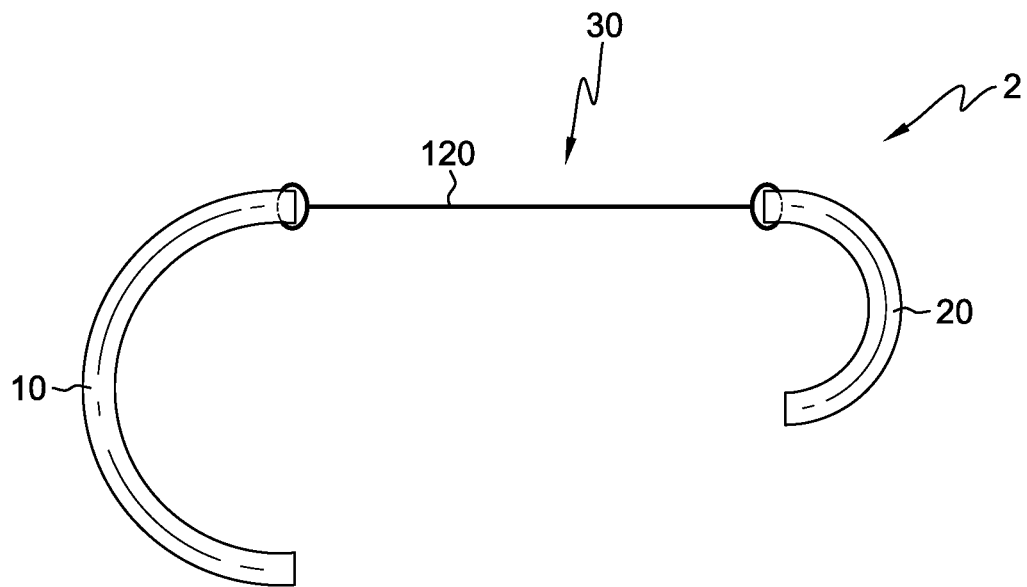
FIG. 19A depicts another embodiment of an implant including a flexure feature.
Figure 19B:
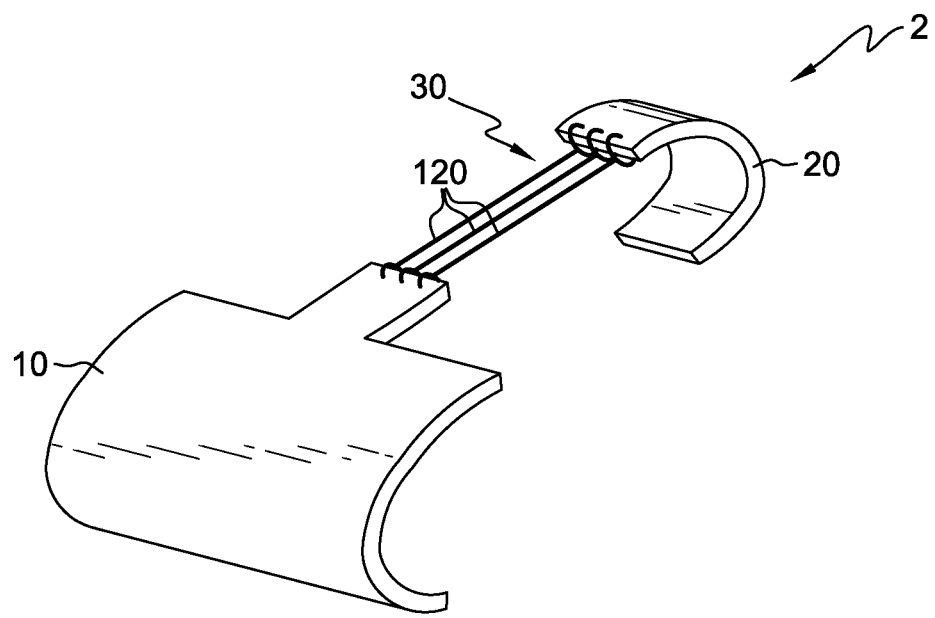
FIG. 19B depicts a top perspective view of FIG. 19A.

In yet another embodiment, shown in FIGS. 18A-18B, the flexure feature 110 includes a region of flexible material. The flexure feature 110 is made of a material that is more flexible than that of the bone engaging features 10 and 20. The flexure feature 110 may permit the implant to flex in the dorsal-plantar direction. Alternatively or in addition, the flexure feature 110 may permit the implant to elongate and/or shorten in the lateral-medial direction.

In yet another embodiment, shown in FIGS. 19A-21, the flexure feature includes cables. In the embodiments shown in FIGS. 19A-20B, the cables may allow the first and second bone engaging features 10, 20 to rotate, translate and twist relative to one another. In embodiments where the flexure feature includes shorter cables, such as the embodiment shown in FIG. 21, the cables 140 may only permit rotational movement between the first and second bone engaging features. In some cases, however, shorter cables may permit rotation and some, but limited, translation and/or twisting between the first and second bone engaging features.

It should be appreciated that other flexure feature arrangements are possible. For example, the flexure feature may be an accordion-like arrangement, a sliding mechanism, may be stamped, may be bendable, may be thinner than the rest of the implant in a direction that is not limited to the dorsal-plantar direction, may have one or more reliefs, may have one large cutout in the center of the intermediate portion, leaving two side rails of material, may be a chain of links, a hinge, or any other suitable arrangement, as this aspect is not so limited.

According to one aspect, the inclusion of one or more flexure features may impart 1, 2, 3, 4, 5 or 6 degrees of freedom to the implant. Depending on the type of flexure feature that is used, in some cases, an implant with additional flexure features may impart additional degrees of freedom to the implant. For example, the embodiment shown in FIGS. 14A and 14B includes one flexure feature 100 that imparts one degree of freedom: rotation about flexure feature 100. The embodiment shown in FIGS. 16-17B includes two flexure features 104, 106 that impart two degrees of freedom to the implant. FIG. 17A depicts the first degree of relative movement: rotation about flexure feature 104. FIG. 17B depicts the second degree of relative movement: rotation about flexure feature 106. As a result, first and second bone engaging features 10, 20 are able to rotate and translate relative to one another.

It should be appreciated that flexure features may be located at any suitable position along the implant. For example, in some embodiments where only one flexure feature is used, the flexure feature may be located closer or further away from the first bone engaging feature 10 than shown in the embodiment seen in FIGS. 14A and 14B. As another example, in some embodiments where two flexure features are used, flexure features may be located closer or further away from one another and/or from the first bone engaging feature 10 than shown in the embodiment seen in FIG. 16.

In some cases, however, a single flexure feature can impart any number of degrees of freedom to the implant. For example, in the embodiment shown in FIGS. 18A and 18B, the flexible material of flexure feature 110 may have any one or any combination of the following capabilities: flex in the dorsal-plantar direction, elongate in the lateral-medial direction, shorten in the lateral-medial direction, twist in the distal-proximal direction, or deform in any other suitable manner.

In other embodiments, as seen in FIGS. 19A-20B, the flexure feature may include cables that impart multiple degrees of freedom. In the embodiment seen in FIGS. 19A-19B, cables 120 may permit rotation, translation and twisting of the first and second bone engaging features 10, 20 relative to one another. In some embodiments, the cables are stretchable to impart an additional degree of freedom. In other embodiments, the cables cannot be stretched. It should be appreciated that any suitable number of cables may be used, as this aspect is not so limited. In one embodiment, depicted in FIG. 20A, flexure features 130 may be one continuous loop, with one end of the loop being coupled to bone engaging feature 10 and the other end of the loop being coupled to bone engaging feature 20. In other embodiments, instead of one continuous loop, the flexure features 140 may be two separate strands that are coupled to the bone engaging features.

In some cases, the length of the cable may impact the degrees of freedom imparted to the implant. In some embodiments, longer cables such as those shown in FIGS. 19A-20B may be used to provide more than a single degree of freedom of relative movement between the first and second bone engaging features. On the other hand, in some embodiments, shorter cables may be used to restrict movement between the first and second bone engaging features to impart a single degree of freedom to the implant. In one embodiment, depicted in FIG. 21, implant 2 includes flexure features 140 in the form of short cables, creating a hinge-like connection.

It should be appreciated that the implant may have any suitable number of degrees of freedom, as this aspect is not so limited. Any suitable number of flexure features may be included and flexure feature(s) of any length may be used.

Figure 20A:
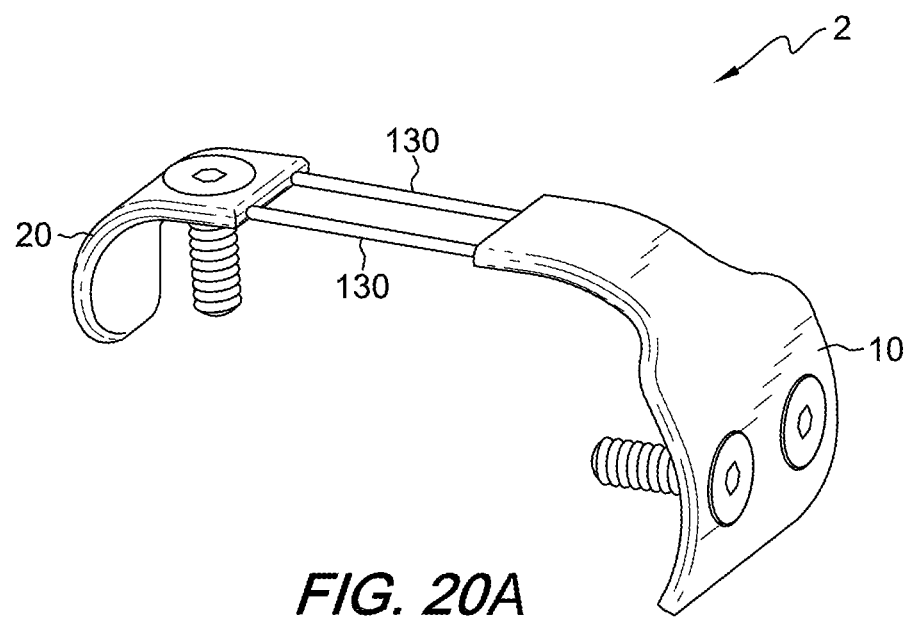
FIG. 20A depicts another embodiment of an implant including a flexure feature.
Figure 20B:
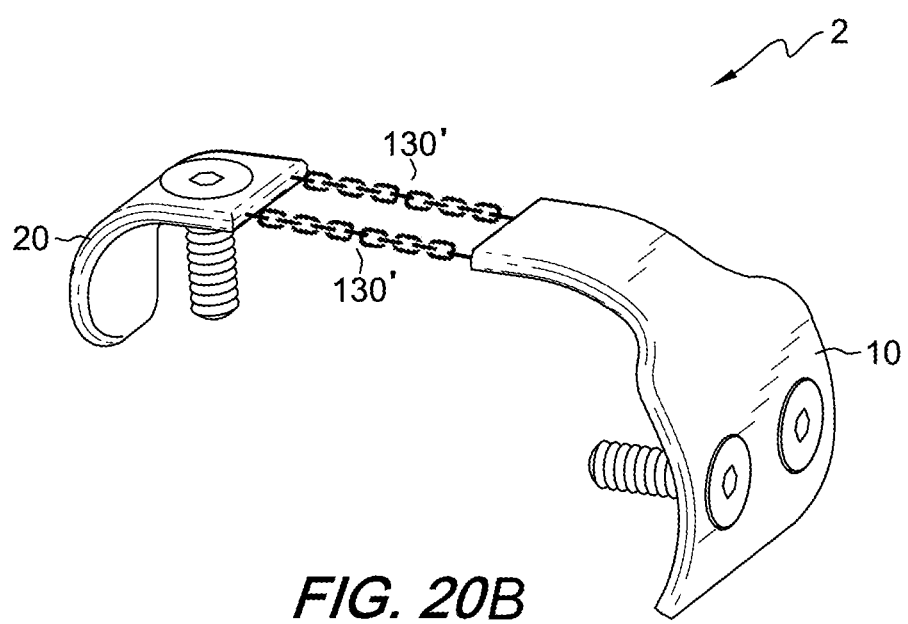
FIG. 20B depicts another embodiment of an implant including a flexure feature.
Figure 21:
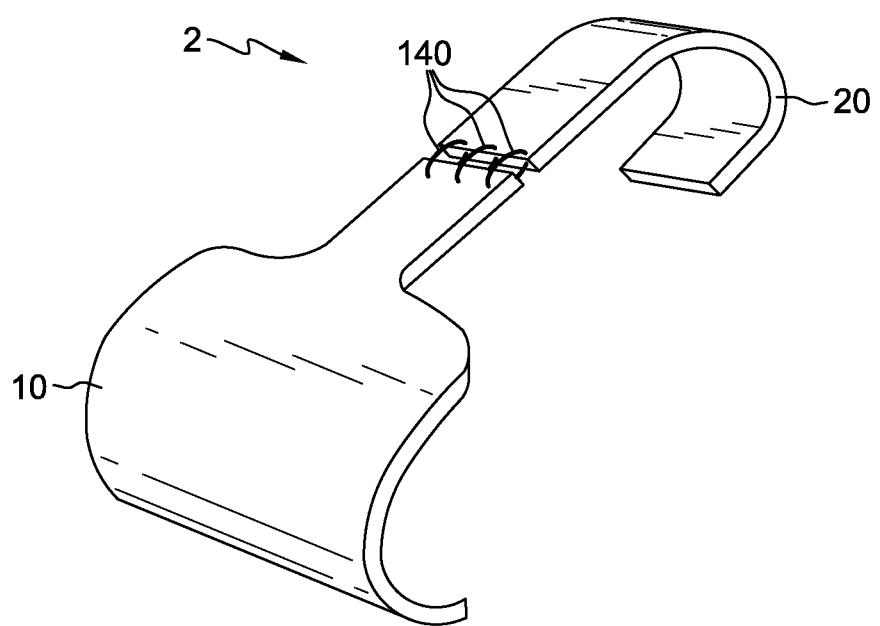
FIG. 21 depicts yet another embodiment of an implant including a flexure feature.

According to one aspect, in some embodiments, the flexure feature may be configured to limit the maximum distance between the engaged metatarsals so as to prevent the metatarsals from returning to their previous hallux valgus positions. For example, in the embodiment where the flexure feature is a region of flexible material as shown in FIGS. 18A and 18B, flexure feature 110 may be arranged such that it can only be shortened from its natural resting position, not elongated. As another example, in the embodiment where the flexure feature includes one or more cables as shown in FIGS. 19A-21, the cables may be non-stretchable, thereby limiting the maximum distance between the engaged metatarsals. The flexure feature may be a chain of links 130', as shown in FIG. 20B, a hinge, a region of decreased depth in the dorsal-plantar direction or other suitable arrangement that permits the bone engaging features 10 and 20 to move toward one another, but restricts movement of the bone engaging features 10 and 20 away from one another beyond a maximum distance. In some embodiments, the flexure feature may be stretchable from its natural resting position, but the flexure feature has a maximum elongation length that prevents the metatarsals from returning to their previous hallux valgus positions.

The flexure feature may be coupled to the implant by any suitable means. In some embodiments, the flexure feature may be coupled to the implant by bonding, adhesive, soldering, welding, physical interlock, clamping, embedding at least one or more portions of the flexure feature within the implant, threading the flexure feature through holes in the implant, mechanical attachment, by being integrally formed with the implant as one monolithic structure, by being stamped into the implant, cutout from the implant, or by any other suitable arrangement, as this aspect is not so limited. As non-limiting, illustrative examples, the ends of flexure features 130 in the embodiment shown in FIG. 20A may be embedded within, welded to or otherwise coupled to first and second bone engaging features 10 and 20. In the case where flexure feature 130 is one continuous loop rather than two independent cables, the ends of the loop may be embedded within, welded to, or otherwise coupled to first and second bone engaging features 10 and 20.

The flexure feature may be made of titanium, nickel, nickel titanium alloy, nitinol or other shape-memory alloy, silver, gold, plastic, an elastomer, metal, metal alloy, stainless steel, a suture, FIBERWIRE, which is a multi-strand, long chain ultra-high molecular weight polyethylene (UHMWPE) core with a braided jacket of polyester and UHMWPE, or any other suitable material, as this aspect is not so limited. The flexure feature may be made from the same material as the rest of the implant or from a different material.

According to one aspect, the flexure feature may be located on only one side of the engaged bones. In some embodiments, where the implant is used in a foot, the flexure feature may be located substantially only dorsal to the metatarsals, such that the flexure feature is located at a height that is positioned above the metatarsals, as opposed to a height that is between the metatarsals or below the metatarsals. In other embodiments, the flexure feature may be located substantially only ventral to the metatarsals, such that flexure feature is located at a height that is positioned below the metatarsals, as opposed to a height that is between the metatarsals or above the metatarsals. The word "substantially" is used to include arrangements where the flexure feature bows slightly inward toward the space between the engaged metatarsals or is otherwise arranged such that a portion of the flexure feature is located at a height that is between the metatarsals. "Substantially only dorsal to or substantially only ventral to the metatarsals" includes such arrangements where a portion of the flexure feature is located at a height that is between the metatarsals.

Figure 22:
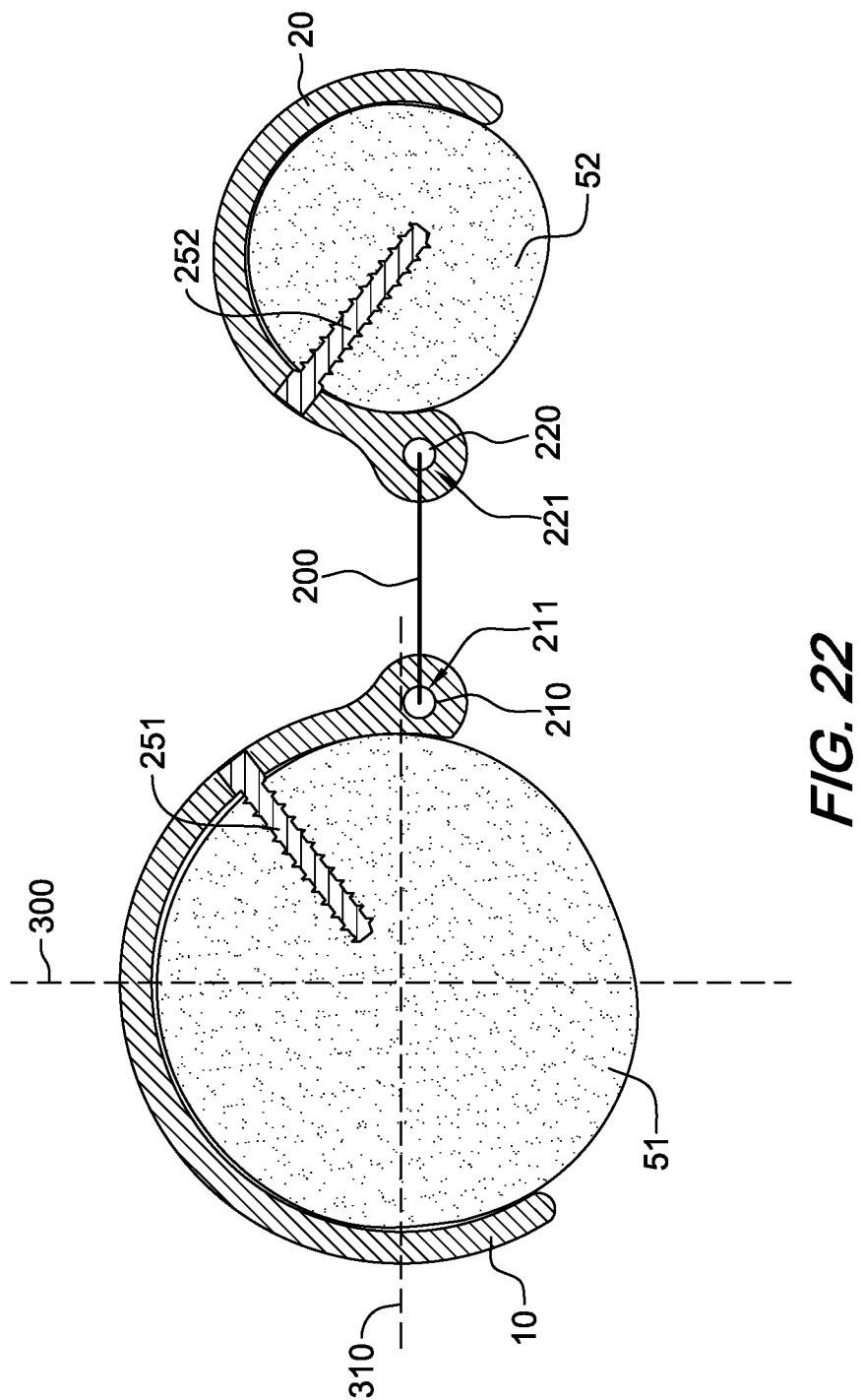
FIG. 22 depicts an embodiment of an implant in accordance with an aspect of the invention.
Figure 23:
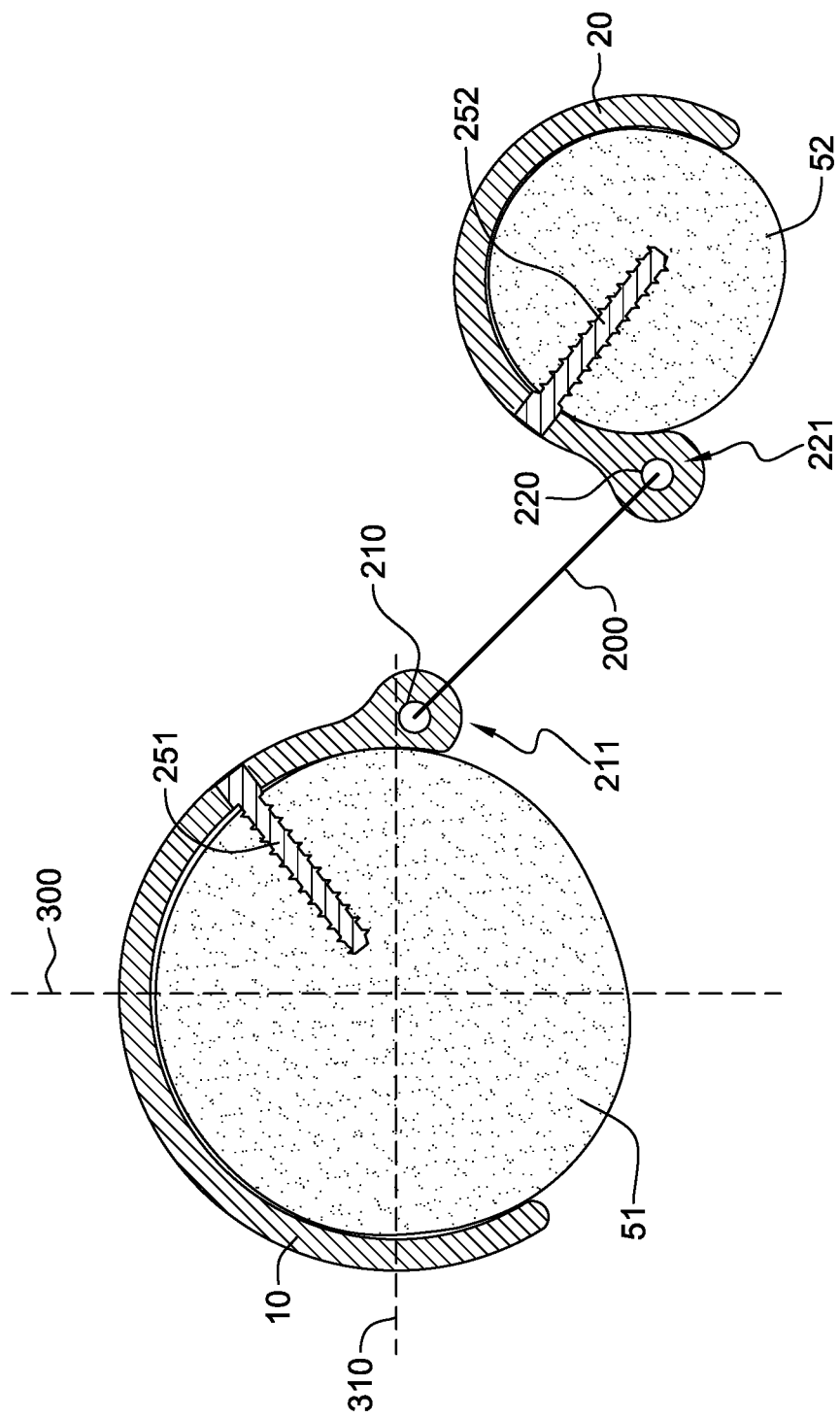
FIG. 23 depicts relative movement of first and second bone engaging features of the implant of FIG. 22.
Figure 24:
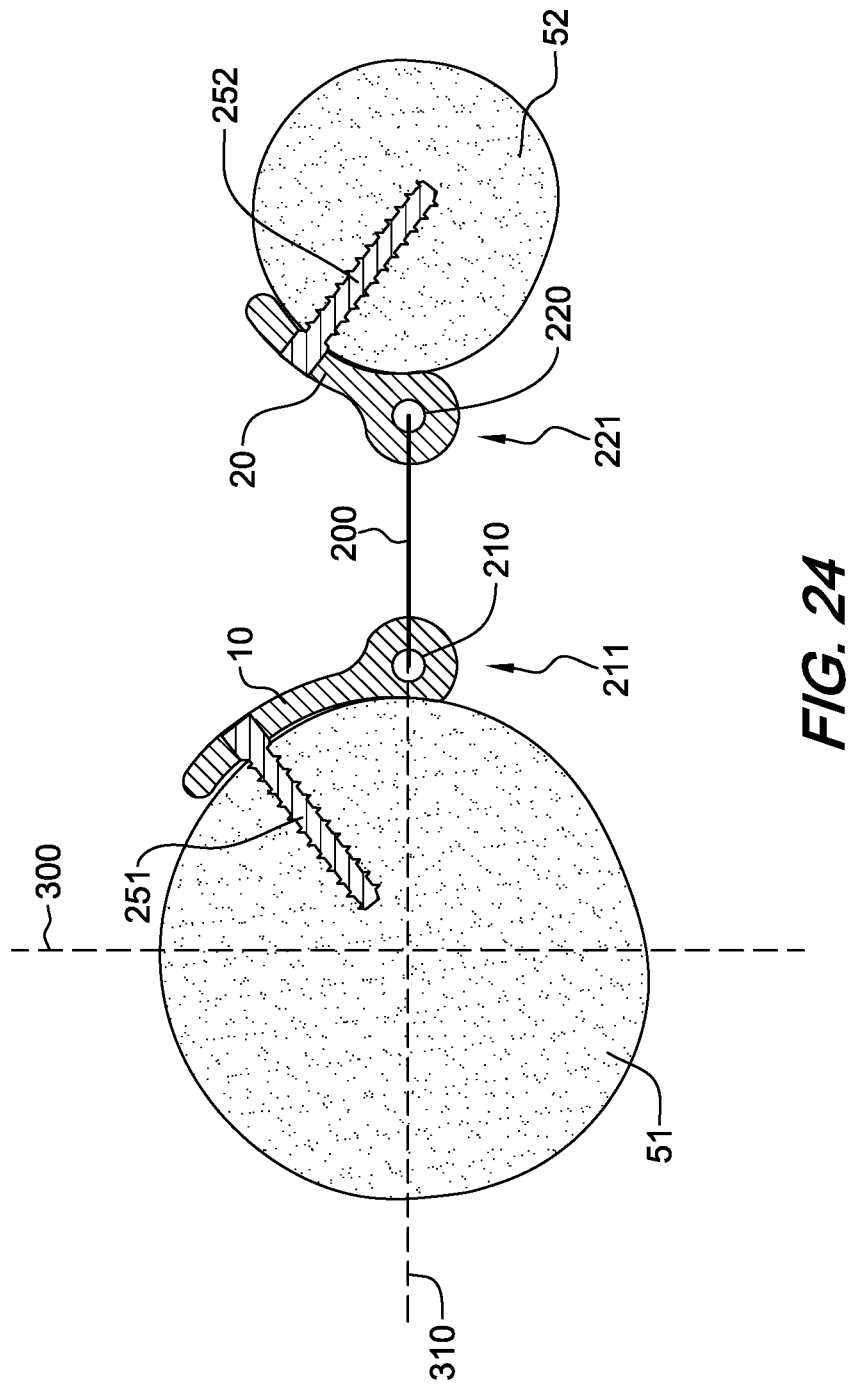
FIG. 24 depicts another embodiment of an implant.

The inventors have recognized that passing portions of an implant completely through a bone may decrease the structural integrity of the bone. As such, according to one aspect, the implant is configured to engage with two bones such that an intermediate portion of the implant is positioned substantially between two bones without any portion of the device (including bone anchors associated with the device) passing completely through either of the bones. As seen in FIGS. 22-24, an intermediate portion 200 of the implant (which also serves as a flexure feature) is positioned substantially between two metatarsals 51, 52, but no part of the implant passes completely through either bone.

In FIG. 22, a first bone engaging feature 10 is wrapped partially around a first metatarsal 51 and a second bone engaging feature 20 is wrapped partially around a second metatarsal 52. A flexure feature 200 couples the first bone engaging feature 10 to the second bone engaging feature 20. In such an arrangement, when the implant is engaged to the first and second bones 51, 52, the intermediate portion 200 is positioned substantially between the bones 51, 52 without passing through the bones. Further, no portion of the implant, including any associated bone anchors, passes completely through either of the bones 51, 52.

The flexure feature 200 may couple to the bone engaging features at coupling points 211, 221 on the bone engaging features. In some embodiments, the bone engaging features may include holes 210, 220 through which the flexure feature may pass. The flexure feature 200 may couple to the bone engaging features by passing through a hole 210 of the first bone engaging feature 10 and a hole 220 of the second bone engaging feature. For example, in one embodiment, the flexure feature 200 is passed through the holes 210, 220 and the flexure feature includes a continuous loop (for example, the ends of the flexure feature may be tied to one another or otherwise attached to one another. In other embodiments, the flexure feature 200 may attach to the coupling points 211, 221 on the bone engaging features 10, 20 through the holes 210, 220 by an arrangement such as a knot, a cow hitch, via an adhesive, by welding, mechanical interlock, or by any other suitable arrangement.

In some embodiments, when the implant is engaged to the two metatarsals, the coupling portion 211 of the first bone engaging feature 10 is positioned near or substantially aligned with the horizontal plane 310 that bisects the first metatarsal through the lateral and medial aspects of the metatarsal. Similarly, the coupling portion 210 of the second bone engaging feature 20 may be positioned near or substantially aligned with a horizontal plane that bisects the second metatarsal through the lateral and medial aspects of the metatarsal. In some embodiments, when the implant is engaged to the two metatarsals, the intermediate portion 200 is positioned near or substantially along the horizontal plane 310 that bisects one of the metatarsals through the lateral and medial aspects of the metatarsal. In some embodiments, the intermediate portion 200, which may serve as or include a flexure feature (such as a cable or wire), the intermediate portion is only in tension and positioned substantially between the bones engaged by the device.

As discussed previously, a flexure feature may permit the metatarsals that are engaged by the implant to move relative to one another after the implant has been implanted. As seen in FIG. 23, the flexure feature 200 may permit translation and/or rotation of the bone engaging features 10, 20 relative to one another. In FIG. 23, the second metatarsal 52 and second bone engaging feature 20 have moved slightly downwardly relative to first metatarsal 51 and first bone engaging feature 10.

When the implant is implanted into the body, the first bone engaging feature 10 is located between the dorsal side of the first metatarsal 51 and the dorsal fascia of the foot, and the second bone engaging feature 20 is located between the dorsal side of the second metatarsal 52 and the dorsal fascia of the foot. In some embodiments, anchor holes are positioned on the bone engaging features such that the bone anchors can be inserted through the bones to attach the bone engaging feature to the bone. The first bone engaging feature 10 may include an anchor hole for receiving a first bone anchor 251, and the second bone engaging feature 20 may include an anchor hole for receiving a second bone anchor 252. Each bone anchor may be inserted through an incision in the dorsal fascia. In some embodiments, one or both of the bone anchors 251, 252 are monocortical anchors—i.e., the anchor penetrates through the metatarsal cortex only once (e.g., through the dorsal cortex), instead of penetrating through the cortex twice.

Figure 25:
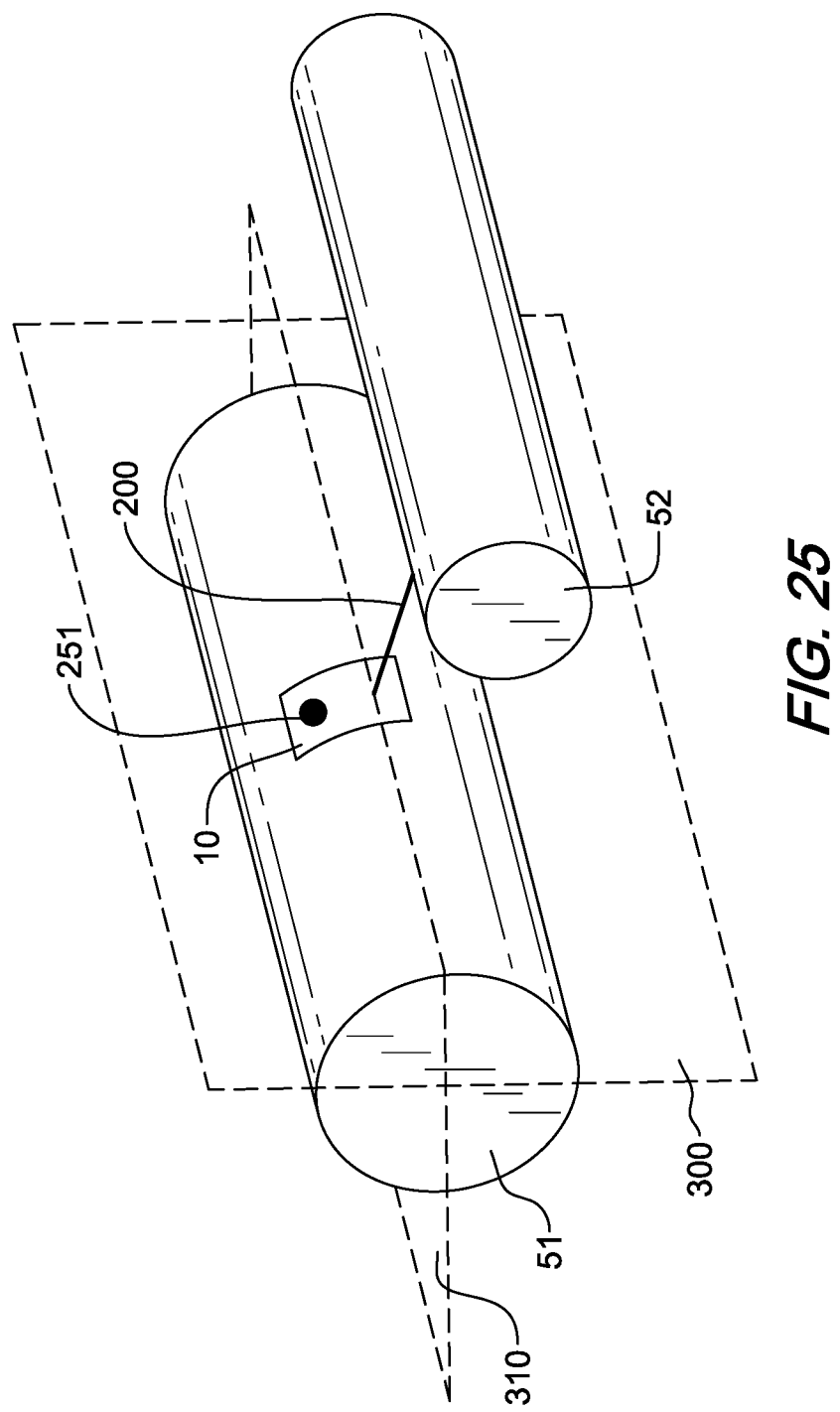
FIG. 25 depicts a perspective view of the embodiment of FIG. 24.

According to one aspect, the implant may be constructed and arranged to couple substantially only to bone aspects that face one another. For example, as shown in FIGS. 24-25, which depicts the first and second metatarsals of the left foot, the first bone engaging feature 10 is coupled substantially only to the lateral aspect of the first metatarsal 51, and the second bone engaging feature 20 is coupled substantially only to the medial aspect of the second metatarsal 52. In other words, the bone engaging features 10, 20 are coupled substantially only to metatarsal aspects that face one another (the lateral aspect of the first metatarsal faces the medial aspect of the second metatarsal.) The words "substantially only to the medial/lateral aspect" include arrangements where a bone engaging feature also couples to a portion of the dorsal side or ventral side of the bone. As seen in FIGS. 24-25, where the implant is constructed and arranged to couple substantially only to bone aspects that face one another, the bone engaging features 10, 20 may be coupled to one another via an intermediate portion 200. In other embodiments, the implant may be constructed and arranged to couple only to bone aspects that face one another, such that the bone engaging feature does not couple to the dorsal or ventral sides of the bones. A bone anchor 251 may be used to attach the first bone engaging feature 10 to the first metatarsal 51 and a second bone anchor 252 may be used to attach the second bone engaging feature 20 to the second metatarsal 52. As with the embodiment shown in FIG. 22, when the implant is engaged to the first and second bones 51, 52, the intermediate portion 200 is positioned substantially between the bones 51, 52 without passing through the bones. Further, no portion of the implant, including any associated bone anchors (such as anchors 251, 252), passes completely through either of the bones 51, 52. In some embodiments, the intermediate portion 200 may include or serve as a flexure feature such as a cable, wire or elastic member. As discussed previously, the flexure feature 200 may couple to coupling points 211, 221 of the bone engaging features 10, 20 via holes 210, 220 in the bone engaging features. In the embodiment shown in FIGS. 24-25, only a single bone anchor 251 is used to attach the first bone engaging feature 10 to the first metatarsal 51.

Figure 26:
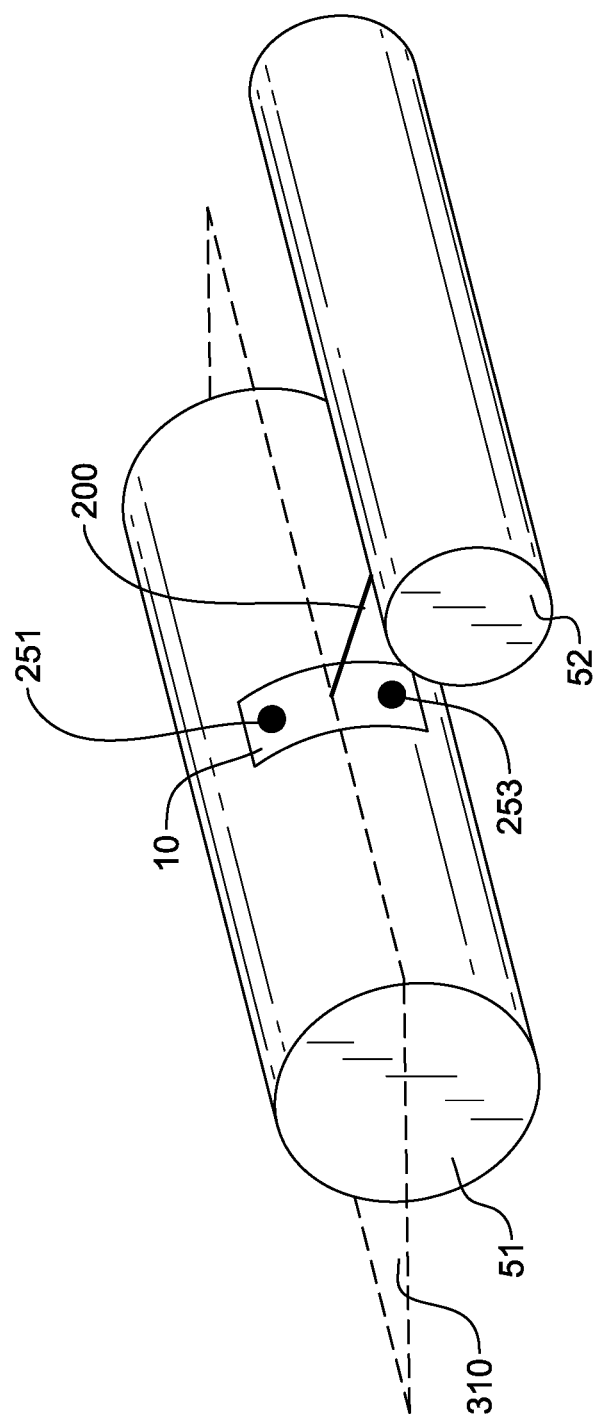
FIG. 26 depicts another embodiment of an implant.
Figure 27:
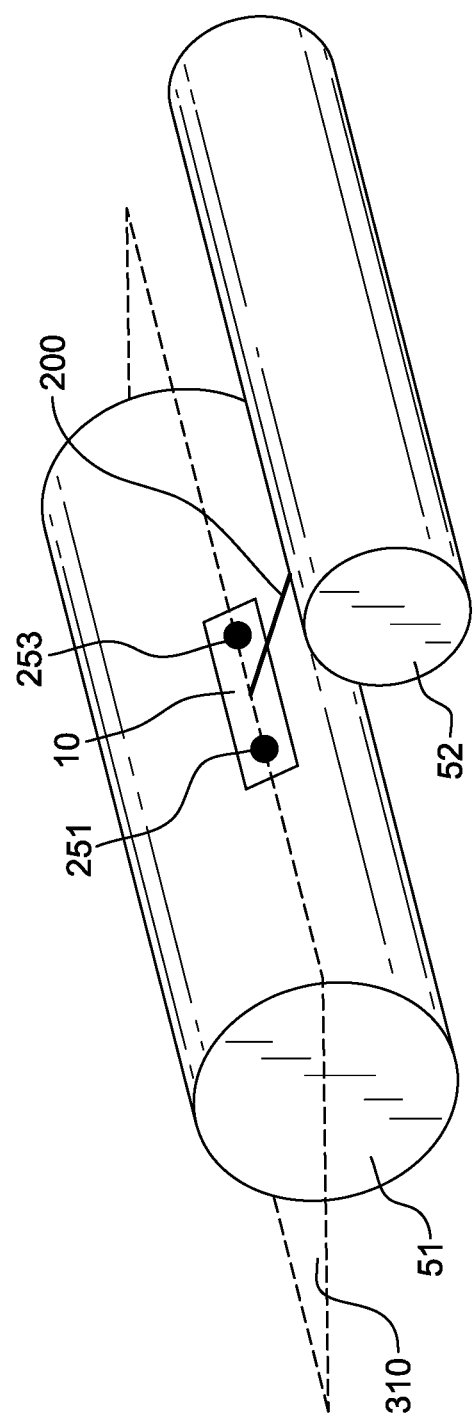
FIG. 27 depicts another embodiment of an implant.

In other embodiments, such as the embodiments shown in FIGS. 26-27, a plurality of bone anchors 251, 253 may be used to attach the first bone engaging feature 10 to the first metatarsal 51. In each of the embodiments shown in FIGS. 26-27, the implant is also constructed and arranged to couple substantially only to bone aspects that face one another. In each of the embodiments, the first bone engaging feature 10 is coupled substantially only to the lateral aspect of the first metatarsal 51, and a second bone engaging feature is coupled substantially only to the medial aspect of the second metatarsal 52. In the embodiment shown in FIG. 26, the bone engaging feature 10 extends along the circumference of the bone such that one anchor 251 is positioned above the horizontal plane 310 and one anchor 253 is positioned below the horizontal plane 310. In FIG. 27, the bone engaging feature 10 extends along the length of the bone such that the anchors 251, 253 are substantially aligned in a direction that is parallel to the horizontal plane 310.

The inventors have recognized that one common failure mode for some bone anchors (such as bone screws) is due to shear loads, and that arranging bone anchors to bear loads in tension may help to decrease the occurrence of such failure modes. The inventors have also recognized that arranging bone anchors to be placed in the body in a position and orientation that is the most easily accessible to a medical practitioner may help to decrease procedure time and risks of complications. The inventors have appreciated that arranging bone anchors to bear loads in tension may result in the bone anchors being positioned and/or oriented in a manner that is not easily accessible to a medical practitioner. As such, the inventors have appreciated the need for a balance between these two considerations. According to one aspect of the invention, bone anchors used to attach the implant to the metatarsals are angled in a manner that decreases shear loads on the bone anchors, while simultaneously being accessible by a medical practitioner.

As seen in each of the illustrative embodiments shown in FIGS. 22-24, the anchors 251, 252 are arranged at an angle relative to a vertical plane 300 that bisects one of the metatarsals through the dorsal and ventral sides of the metatarsal. In some embodiments, such an angle may be accomplished by arranging anchor holes on the bone engaging features at a position such that the bone anchors can be inserted through the bones at an angle relative to the vertical axis 300. In other words, in some embodiments, an anchor hole is positioned on a portion of a bone engaging feature that is constructed and arranged to contact or be positioned close to a portion of the bone that is angled away from the vertical plane 300. Such an angle may be achievable by a medical practitioner when inserting the anchor, and/or may allow the medical practitioner to access the anchor if the anchor requires removal. In addition, such an angle may help to decrease the shear loads that the anchor is subjected to. In some embodiments, the bone anchors may be substantially parallel to a horizontal plane 310 that bisects one of the metatarsals through the lateral and medial aspects of the metatarsal. In some embodiments, when the implant device is engaged with the metatarsals, the bone anchors are substantially parallel to the flexure feature 200, which may be a wire. While this aspect discusses positioning anchors at an angle relative to the vertical plane, it should be appreciated that, in other embodiments, the bone anchors may be substantially parallel to the vertical plane 300. In some embodiments, the bone anchors 251, 252 may be located as closely as possible to the coupling points 211, 221 of the bone engaging features 10, 20.

According to certain aspects of the invention, a surgical procedure is used to deploy the implant. In some embodiments, when treating a patient with hallux valgus, a standard medial approach for hallux valgus repair may be employed. During the procedure, the surgeon may perform a complete lateral release either through a separate distal approach or through the medial incision. A small incision may be placed just lateral to the second metatarsal, thereby exposing the metatarsal. A fascial elevator may be inserted from the medial aspect of the first metatarsal just proximal to the metaphysis, extending to the lateral aspect of the second metatarsal. As a result, the soft tissue may be elevated to form an envelope. The surgeon may then choose an appropriately sized implant based on the patient's anatomical characteristics. The implant may be inserted into the space provided by the fascial elevator, and may be placed around the second metatarsal. The first metatarsal may then be manually reduced, and the implant may be secured to the first metatarsal with locking or non-locking bone screws or other suitable bone engaging feature. Bone screws or other hardware may be drilled just through the cortex of the bone to a depth of about 1 mm, without fully penetrating through the entire bone. As illustrated in FIGS. 3 and 9, in one embodiment, bone screws or other hardware may be inserted though bone anchor holes 16. An additional screw may be secured dorsally into the second metatarsal. As illustrated in FIG. 9, in one embodiment, the additional screw may be inserted through dorsal bone anchor hole 26. In some embodiments, treatment of tailor's bunion may employ a similar procedure. Of course, it should be appreciated that the present invention is not limited in this respect and other suitable procedures may be employed.

Figure 28:
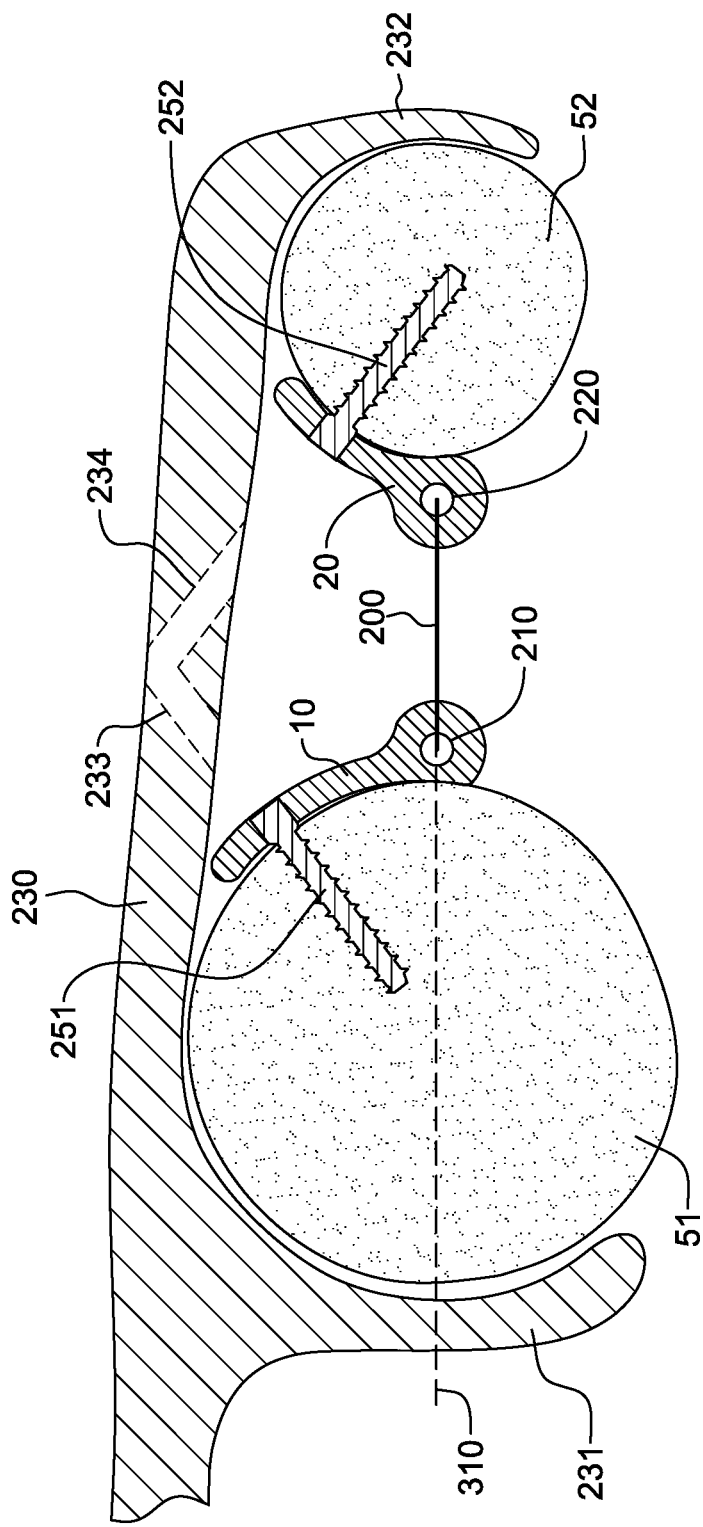
FIG. 28 depicts an instrument used to deploy the implant in accordance with an aspect of the invention.

According to one aspect, a specially configured instrument may be used to deploy the implant. The instrument may have a clasping mechanism that provides a holding force to keep the metatarsals of interest parallel to each other or in any other desirable configuration while the implant is coupled to the metatarsals. In some embodiments, the instrument holds the metatarsals of interest in place while anchors are used to couple the implant to the metatarsals. As the bone anchors engage metatarsals, the instrument is disengaged from the metatarsals. In one illustrative embodiment, shown in FIG. 28, an instrument 230 has two clasping members 231, 232 that provide a holding force on the metatarsals 51, 52 to keep the metatarsals at a set distance from one another and/or parallel to each other, or in any other desirable configuration while an implant is coupled to the metatarsals. In some embodiments, the instrument 230 has passages 233, 234 through which anchors 251, 252 can be passed such that the anchors 251, 252 can be used to attach the implant to the metatarsals. Once the anchors are in place, the instrument 230 can be disengaged from the metatarsals 51, 52.

According to one aspect, the implant may be positioned on the dorsal side of the metatarsal bones. Alternatively, the implant may be positioned on the ventral side of the metatarsals. Positioning of the implant on the dorsal side of the metatarsals may be preferred due to improved patient comfort and less interference with daily activities. In addition, deployment of the implant on the dorsal side of the metatarsals may require a less invasive surgical procedure.

According to one aspect, depending on the extent of the deformity (e.g. large intermetatarsal angle), the implant may be used as an adjunctive device in combination with an additional surgical procedure. Surgical procedures include wedge osteotomy, trans-positional osteotomy, fusion, joint replacement, or other suitable surgical procedure, as this aspect is not limited in this regard.

In some embodiments, the implant may remain permanently within the body. In some cases, the implant may be replaced after a certain amount of time. In others, the implant may be bioabsorbable or may be removed after a certain amount of time.

In some embodiments, the implant may be constructed of any biocompatible material such as titanium, nickel, nickel titanium alloy, nitinol or other shape-memory alloy, silver, gold, plastic, or other suitable material. In some embodiments, the material may be substantially rigid, as opposed to elastic. In other embodiments, the material may be elastic. In some cases, the material may be substantially deformable by hand. The implant may be formed from a plate or strip of material that is about 0.7 to about 1.2 millimeters thick and about 5 to about 15 millimeters wide.

According to one aspect, the implant may be formed using any suitable process. The implant may be stamped out of sheet metal or cast from metal and curved at each end by a plate bender or other suitable tool. Any suitable finishing and/or sterilization processes may be applied to the implant, as this aspect is not limited in this regard.

According to one aspect, the implant may have permanent discrete lengths, widths and/or thicknesses. In some embodiments, a range of implants of different sizes may be provided in a kit. For example, in one embodiment, the kit may include a range of five discretely sized implants or implant systems: the first may be suitable for very small patients, the second may be suitable for patients who are somewhat smaller than average, the third may be suitable for average-sized patients, and so on, where the size range of implants or implant systems is linearly scaled. In some embodiments, the first implant may have a length of about 32 mm, the second may have a length of about 34 mm, the third implant may have a length of about 36 mm, the fourth implant may have a length of about 38 mm, and the fifth implant may have a length of about 40 mm. In some embodiments, kits may be designed to suit a specific gender, age, and/or severity of deformity. For example, kits for pediatric applications may include smaller implants than kits for adult applications. In some embodiments, kits may also include instruments used to adjust the implants, such as a plate bender. Of course, it should be appreciated that the present invention is not limited in this respect and other suitable kits may be employed. For example, the kits may include any number of implants at any range of sizes. In another embodiment, each discretely-sized implant may be provided individually rather than in a collective kit.

The above aspects may be employed in any suitable combination, as the present invention is not limited in this respect. Also, any or all of the above aspects may be employed in an implant; however, the present invention is not limited in this respect, as the above aspects may be employed with other medical devices.

Also, as described herein, the surgical implant may be used for correction of hallux valgus or tailor's bunion. However, embodiments of the invention are not limited to use for correction of hallux valgus, tailor's bunion, or deformities of the foot bones. According to some aspects, the surgical implant may be used in other locations of the body, for example, with the metacarpals of the hand, the radius and ulna of the arm, or the fibula and tibia of the leg, etc., as aspects are not limited in this regard. In addition, while some embodiments of the invention disclosed herein may discuss use of a surgical implant with a human subject, the surgical implant may be used in non-human subjects as well, as the invention is not limited in this regard.

Having thus described several aspects of at least one embodiment of this invention, it is to be appreciated various alterations, modifications, and improvements will readily occur to those skilled in the art. For example, the surgical implant described herein may be adapted for placement in other locations. Such alterations, modification, and improvements are intended to be part of this disclosure, and are intended to be within the spirit and scope of the invention. Accordingly, the foregoing description and drawings are by way of example only.

What is claimed is:

1. An implant for repositioning bones of a patient to a more anatomically correct position, the implant comprising:
    a first bone engaging feature with a first end opposite a second end and a first side opposite a second side, wherein at least one first width extends between the first side and the second side, and wherein the first end of the first bone engaging feature is shaped to wrap partially around a first bone;

a second bone engaging feature with a first end opposite a second end and a first side opposite a second side, wherein a second width extends between the first side and the second side, wherein the second end of the second bone engaging feature is shaped to wrap partially around a second bone; and an intermediate portion connecting the first and second bone engaging features, wherein the intermediate portion includes a flexure feature that permits relative movement of the first and second bone engaging features, wherein a first portion of the flexure feature engages a first opening in the first bone engaging features near the first side, wherein a second portion of the flexure feature engages a first opening in the second bone engaging features near the first side, wherein a third portion of the flexure feature engages a second opening in the first bone engaging features near the second side, wherein a fourth portion of the flexure feature engages a second opening in the second bone engaging feature near the second side, wherein the first portion is spaced apart from the third portion and the second portion is spaced apart from the fourth portion, wherein the first opening in the first bone engaging feature is separated and spaced apart from the second opening in the first bone engaging feature, wherein the first opening in the second bone engaging feature is separated and spaced apart from the second opening in the second bone engaging feature, wherein the first opening and the second opening of the first bone engaging feature are positioned at the second end of the first bone engaging feature, wherein the first opening and the second opening of the second bone engaging feature are positioned at the first end of the second bone engaging feature, wherein at least one of the first portion and the third portion of the flexure feature are directly coupled to at least one of the first opening and the second opening of the first bone engaging feature;

wherein at least one of the second portion and the fourth portion of the flexure feature are directly coupled to at least one of the first opening and the second opening of the second bone engaging feature; and wherein a first width of the at least one first width is larger than the second width.

2. The implant of claim 1, wherein the intermediate portion also includes a first remaining portion of the first bone engaging feature that surrounds the first and second openings of the first bone engaging feature and a second remaining portion of the second bone engaging feature that surrounds the first and second openings of the second bone engaging feature, and wherein the flexure feature has a dorsal-plantar depth that is less than a dorsal-plantar depth of the first and second remaining portions of the intermediate portion.

3. The implant of claim 2, wherein the flexure feature has a distal-proximal width that is less than or equal to a distal-proximal width of the first and second remaining portions of the intermediate portion.

4. The implant of claim 1, wherein the intermediate portion also includes a first remaining portion of the first bone engaging feature that surrounds the first and second openings of the first bone engaging feature and a second remaining portion of the second bone engaging feature that surrounds the first and second openings of the second bone engaging feature, and wherein the flexure feature is more flexible than the first and second remaining portions of the intermediate portion.

5. The implant of claim 1, wherein the flexure feature is more flexible than the first and second bone engaging features.

6. The implant of claim 1, wherein the flexure feature comprises at least one cable.

7. The implant of claim 6, wherein the cable is stretchable.

8. The implant of claim 6, wherein the cable cannot be stretched.

9. The implant of claim 1, wherein the flexure feature comprises a chain of links.

10. The implant of claim 1, wherein the first and second bones comprise metatarsal bones.

11. An implant for repositioning bones of a patient to a more anatomically correct position, the implant comprising:

a first bone engaging feature including a first end opposite a second end, and at least one first width extending substantially perpendicular to the first end and the second end, wherein the first end of the first bone engaging feature is for engaging a first bone;

a second bone engaging feature including a first end opposite a second end, and a second width extending substantially perpendicular to the first end and the second end, wherein the second end of the second bone engaging feature is for engaging a second bone; and an intermediate portion connecting the first and second bone engaging features, wherein the intermediate portion includes a flexure feature that permits relative movement of the first and second bone engaging features, wherein the flexure feature is arranged such that, when the implant is engaged with the first and second bones, the flexure feature is located between a substantially dorsal surface and substantially a plantar surface of each metatarsal of a foot of the patient, wherein the flexure feature includes a first portion coupled to the first bone engaging feature and the second bone engaging feature near a first side of the implant, wherein the flexure feature includes a second portion coupled to the first bone engaging feature and the second bone engaging feature near a second side of the implant, wherein the first portion is spaced apart from the second portion, wherein at least one of the first portion and the second portion is secured to the first bone engaging feature and wherein at least one of the first portion and the second portion is secured to the second bone engaging feature, and wherein the first and second portions are directly secured to the first and second bone engaging features by at least one of bonding, adhesive, soldering, welding, clamping, embedding, integral formation, stamping, and monolithic formation, wherein the flexure feature is coupled to the second end of the first bone engaging feature, wherein the flexure feature is coupled to the first end of the second bone engaging feature; and wherein a width of the at least one first width at the first end of the first bone engaging feature is larger than the second width.

12. The implant of claim 11, wherein the first bone-engaging feature is designed to wrap partially around the first bone.

13. The implant of claim 11, wherein the intermediate portion also includes a first remaining portion of the first bone engaging feature that surrounds a first opening and a second opening of the first bone engaging feature and a second remaining portion of the second bone engaging feature that surrounds a first opening and a second opening of the second bone engaging feature, and wherein the flexure feature has a dorsal-plantar depth that is less than a dorsal-plantar depth of the first and second remaining portions of the intermediate portion.

14. The implant of claim 13, wherein the flexure feature has a distal-proximal width that is less than or equal to a distal-proximal width of the first and second remaining portions of the intermediate portion.

15. The implant of claim 11, wherein the intermediate portion also includes a first remaining portion of the first bone engaging feature that surrounds a first opening and a second opening of the first bone engaging feature and a second remaining portion of the second bone engaging feature that surrounds a first opening and a second opening of the second bone engaging feature, and wherein the flexure feature is more flexible than the first and second remaining portions of the intermediate portion.

16. The implant of claim 11, wherein the flexure feature is more flexible than the first and second bone engaging features.

17. The implant of claim 11, wherein the flexure feature comprises at least one cable.

18. The implant of claim 17, wherein the cable is stretchable.

19. The implant of claim 17, wherein the cable cannot be stretched.

20. The implant of claim 11, wherein the flexure feature comprises a chain of links.

21. An implant for repositioning bones of a patient to a more anatomically correct position, the implant comprising:
a first bone engaging feature with a first end shaped to engage a first bone, wherein the first bone engaging feature includes a top surface, a bottom surface, a second end positioned opposite the first end, and at least one first width extending perpendicular to a first axis extending between the first end and the second end, wherein the first bone engaging feature includes an arc between the first end and the second end, and wherein the arc is at least 90°;
a second bone engaging feature with a second end shaped to engage a second bone, wherein the second bone engaging feature includes a top surface, a bottom surface, and a first end positioned opposite the second end, and a second width extending perpendicular to a second axis extending between the first end and the second end; and
an intermediate portion connecting the first and second bone engaging features, the intermediate portion comprising:
a first segment coupled to the first bone engaging feature and the second bone engaging feature near a first side of the implant;
a second segment coupled to the first bone engaging feature and the second bone engaging feature near a second side of the implant;
wherein the first segment and the second segment are coupled to the first bone engaging feature at the second end of the first bone engaging feature; and
wherein the first segment and the second segment are coupled to the second bone engaging feature at the first end of the second bone engaging feature;
wherein the intermediate portion is constructed and arranged such that, when the implant is engaged with the first and second bones, the intermediate portion is positioned substantially between the first and second bones without any portion of the implant passing entirely through either the first or second bones,
wherein the intermediate portion includes a top portion and the top portion of the intermediate portion is positioned between the top surfaces and the bottom surfaces of the first bone engaging feature and the second bone engaging feature,
wherein the first segment is separated and spaced apart from the second segment along the entire length as the first and second segments extend between the first bone engaging feature and the second bone engaging feature in a final implanted position; and
wherein a first width of the at least one first width is larger than the second width.

22. The implant of claim 21, wherein the intermediate portion includes a flexure feature that permits relative movement of the first and second bone engaging features.

23. The implant of claim 21, wherein:
the first bone engaging feature has a first coupling portion,
the intermediate portion is constructed and arranged to couple to the first bone engaging feature at the first coupling portion, and
when the implant is engaged with the first and second bones, the first coupling portion is near or substantially aligned with a horizontal plane that bisects the first bone through lateral and medial aspects of the first bone.

24. The implant of claim 23, wherein:
the second bone engaging feature has a second coupling portion,
the intermediate portion is constructed and arranged to couple to the second bone engaging feature at the second coupling portion, and
when the implant is engaged with the first and second bones, the second coupling portion is near or substantially aligned with a horizontal plane that bisects the second bone through lateral and medial aspects of the second bone.

25. An implant for repositioning bones of a patient to a more anatomically correct position, the implant comprising:
a first bone engaging feature shaped to engage a first bone at a first end, the first bone engaging feature having at least one first bone anchor hole constructed and arranged to receive at least one first bone anchor;
a second bone engaging feature shaped to engage a second bone at a second end, the second bone engaging feature having a second bone anchor hole constructed and arranged to receive a second bone anchor; and
an intermediate portion connecting only the first and second bone engaging features,
wherein the second bone anchor hole is positioned on a portion of the first bone engaging feature that is constructed and arranged to be positioned close to a portion of the bone that is angled away from a vertical plane that bisects the first bone through dorsal and plantar sides of the first bone, and
wherein the at least one first bone anchor hole is positioned substantially perpendicular to the second bone anchor hole,
wherein the intermediate portion comprises:

a first portion extending between and engaging the first bone engaging feature on a first end of the first portion and the second bone engaging feature on a second end of the first portion; and a second portion extending between and engaging the first bone engaging feature on a first end of the second portion and the second bone engaging feature on a second end of the second portion;

wherein the first portion is spaced apart from the second portion as the first and second portions extend between the first bone engaging feature and the second bone engaging feature in a final implanted position;

wherein the first ends of the first portion and the second portion of the intermediate portion are coupled to first openings in a second end of the first bone engaging feature;

wherein the second ends of the first portion and the second portion of the intermediate portion are coupled to second openings in a first end of the second bone engaging feature;

wherein the first bone engaging feature includes a first length and at least one first width, wherein the first length is larger than a largest first width of the at least one first width, and wherein the openings of the first bone engaging feature extend into the first bone engaging feature from the second end of the first bone engaging feature perpendicular to each of the first widths of the at least one first width;

wherein the second bone engaging feature includes a second length and a second width, wherein the second length is larger than the second width, and wherein the openings of the second bone engaging feature extend into the second bone engaging feature from the first end of the second bone engaging features perpendicular to the second width; and wherein the largest first width of the at least one first width is larger than the second width.

\* \* \* \* \*